United States Patent
Whayne et al.

(10) Patent No.: US 6,887,192 B1
(45) Date of Patent: May 3, 2005

(54) HEART SUPPORT TO PREVENT VENTRICULAR REMODELING

(75) Inventors: James G. Whayne, San Jose, CA (US); Deborah Tolomeo, San Jose, CA (US); Russell A. Houser, Livermore, CA (US); Sidney D. Fleischman, Menlo Park, CA (US)

(73) Assignee: Converge Medical, Inc., Sunnyvale, CA (US)

( * ) Notice: Subject to any disclaimer, the term of this patent is extended or adjusted under 35 U.S.C. 154(b) by 373 days.

(21) Appl. No.: 09/706,307

(22) Filed: Nov. 3, 2000

Related U.S. Application Data

(60) Provisional application No. 60/231,075, filed on Sep. 8, 2000.

(51) Int. Cl.$^7$ .......................... A61N 1/362; A61M 1/10
(52) U.S. Cl. .......................................... 600/16; 623/3.1
(58) Field of Search .............................. 600/16, 17, 18; 604/65, 66, 67, 503; 623/3.1, 3.11, 3.12, 3.26; 602/36, 37, 75, 76; A61N 1/362; A61M 1/10

(56) References Cited

U.S. PATENT DOCUMENTS

| | | | |
|---|---|---|---|
| 4,621,617 A | | 11/1986 | Sharma |
| 5,713,954 A | | 2/1998 | Rosenberg et al. |
| 5,827,171 A | * | 10/1998 | Dobak et al. ................. 600/16 |
| 5,941,813 A | * | 8/1999 | Sievers et al. ................. 600/16 |
| 6,076,013 A | | 6/2000 | Brennan et al. |
| 6,099,460 A | | 8/2000 | Denker |

FOREIGN PATENT DOCUMENTS

| | | |
|---|---|---|
| DE | 19 826 675 | 3/1999 |
| WO | WO 98/19719 A1 | 5/1998 |
| WO | WO 98/29041 A1 | 7/1998 |
| WO | WO 99/30647 A1 | 6/1999 |
| WO | WO 99/44534 A1 | 9/1999 |
| WO | WO 99/55399 A2 | 11/1999 |
| WO | WO 00/06026 A2 | 2/2000 |
| WO | WO 00/06027 A2 | 2/2000 |
| WO | WO 00/06028 A1 | 2/2000 |
| WO | WO 0016700 A1 | 3/2000 |
| WO | WO 00/18320 A1 | 4/2000 |
| WO | WO 01/67985 A1 | 9/2001 |

* cited by examiner

Primary Examiner—Daniel Robinson
(74) Attorney, Agent, or Firm—Carol M. LaSalle; Bozicevic, Field & Francis LLP

(57) ABSTRACT

This is a support device that prevents, reduces, and delays remodeling of diseased cardiac tissue, and also decreases the impact of such remodeling on collateral tissue is disclosed. The invention further reinforces abnormal tissue regions to prevent over-expansion of the tissue due to increased afterload and excessive wall tension. As a result, the support device prevents phenomenon such as systolic stretch from occurring and propagating. The support structure maintains and restores diastolic compliance, wall motion, and ejection fraction to preserve heart functionality. As such, the support device prevents and treats cardiomyopathy and congestive heart failure.

57 Claims, 13 Drawing Sheets

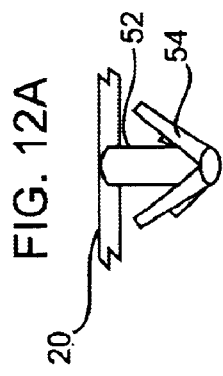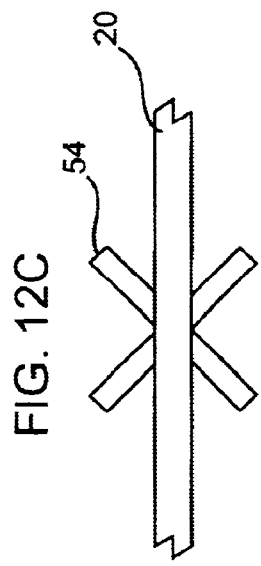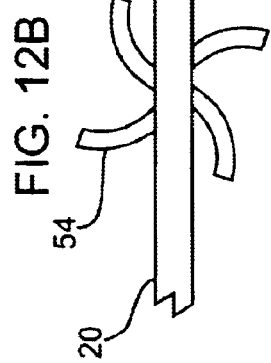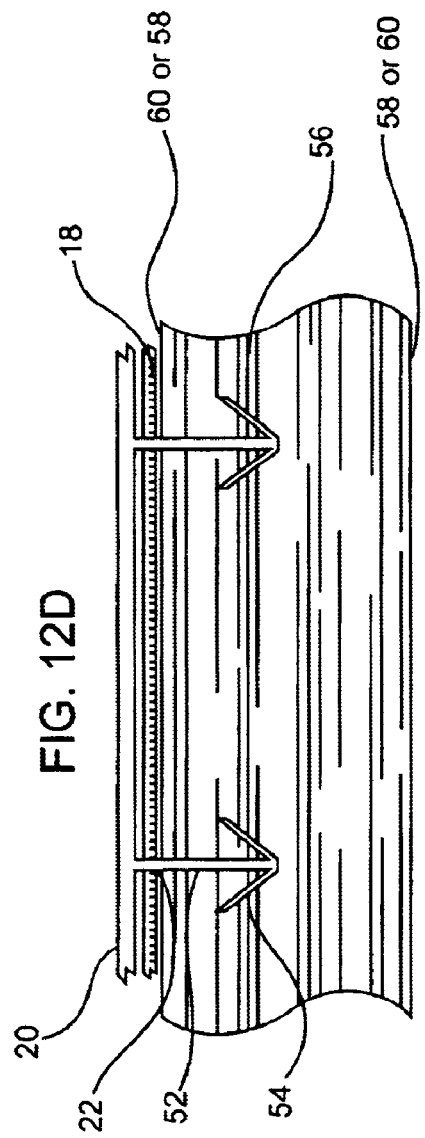

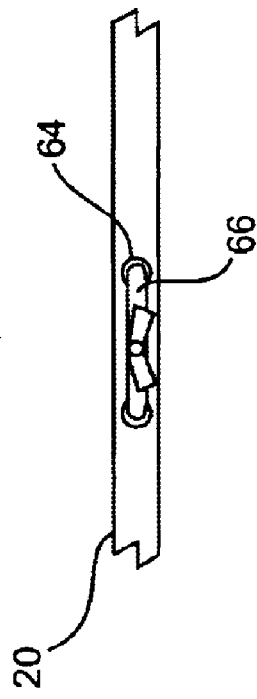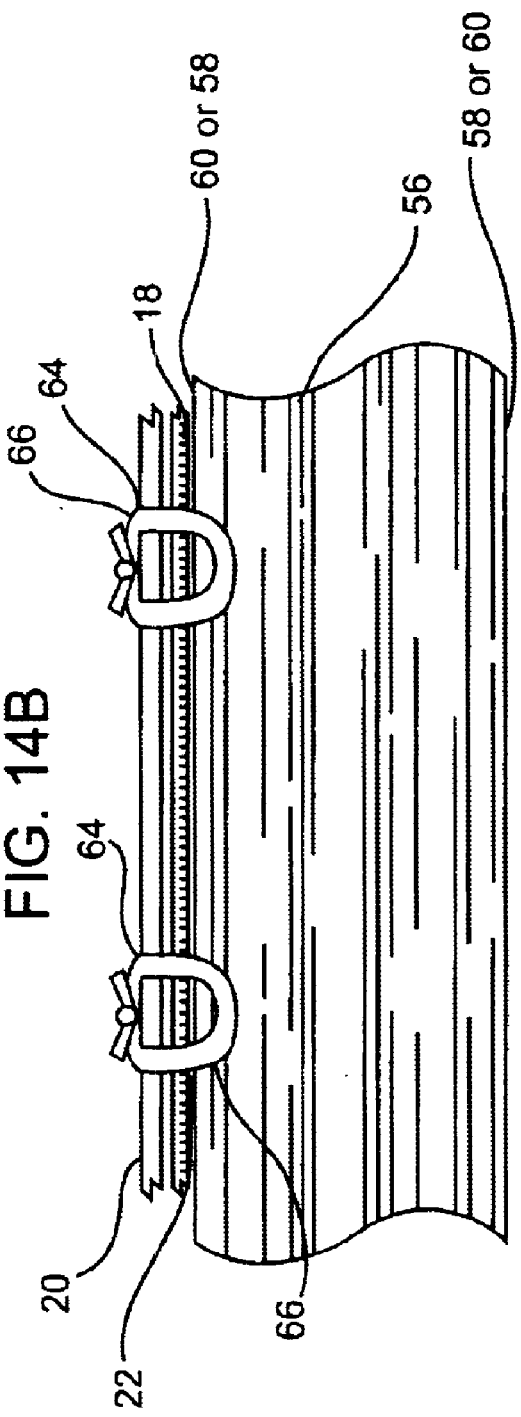

HEART SUPPORT TO PREVENT VENTRICULAR REMODELING

CROSS REFERENCE TO RELATED APPLICATION

This application claims priority to provisional U.S. Patent Application Ser. No. 60/231,075, filed Sep. 8, 2000, the entirety of which is hereby incorporated by reference.

FIELD OF THE INVENTION

This invention is directed towards the transfer of energy from viable tissue regions to less viable or non-viable regions, thereby preventing, compensating for, or treating tissue responses to ischemia, infarction, or other abnormalities. In particular, this invention is directed towards the prevention, reduction, and delay of the remodeling of diseased cardiac tissue and the prevention and treatment of cardiomyopathy and congestive heart failure.

BACKGROUND OF THE INVENTION

Ischemic injury causes tissue remodeling over time. This produces dyssynchronous, hypokinetic, dyskinetic or akinetic tissue function. One mechanism that perpetuates tissue remodeling (termed systolic stretch) occurs when viable ventricular tissue contracts, producing pressure that causes less viable or non-viable tissue to be forced outward. This bulging of the less viable or non-viable tissue dissipates the pumping force of the heart and adversely impacts cardiac output. The heart attempts to compensate for this decrease in cardiac output by increasing contractility and/or heart rate. However, the degree of systolic stretch progressively increases over time, continuing to reduce cardiac output, enlarge the volume of remodeled tissue, and exacerbate the potential for rupture of the affected tissue.

One condition that can result from such remodeling is cardiomyopathy, a typically chronic disorder of heart muscle that may involve hypertrophy and obstructive damage to the heart. A current approach for treating end-stage cardiomyopathy involves resecting a significant portion of the left ventricular free wall to reduce the size of the left ventricular cavity. The procedure, developed by Randas J. V. Batista, attempts to improve the relationship between volume, mass, and diameter. In reducing the volume of the left ventricle, investigators have observed a decrease in mitral regurgitation but a concomitant decrease in diastolic compliance. This decreases diastolic filling, which adversely impacts the complete cardiac cycle.

Other approaches for treating cardiomyopathy include reshaping the heart chambers using tethers, balloons, external bands, or other tension structures to reduce the end-diastolic diameters of the ventricles. PCT Pamphlets WO 98/29041 entitled "Heart Wall Tension Reduction Apparatus and Method"; WO 99/30647 entitled "Valve to Myocardium Tension Members Device and Method"; WO 00/06026 entitled "Heart Wall Tension Reduction Apparatus and Method"; WO 00/06027 entitled "Stress Reduction Apparatus and Method"; WO 00/06028 entitled "Transventricular Implant Tools and Devices"; WO 00/16700 entitled "External Stress Reduction Device and Method" describe tethers or bands that change the geometry of the heart and restrict the maximum outer diameters of the ventricles. The tethers are positioned inside the heart and extend from one side of the ventricle to the other to exert tension on opposite sides of the heart. The bands are positioned around the epicardial surface of the ventricles and restrict expansion of the ventricles. The tethers and bands only limit local wall tension and maximal end-diastolic diameter; they do not directly assist in systolic ejection or diastolic filling of the heart. Nor do they distribute loading over a large region of heart tissue.

SUMMARY OF THE INVENTION

The present invention addresses deficiencies associated with prior approaches of purely reducing the end-diastolic diameter of the heart or preventing over-stressing of cardiac tissue. The approach described by this invention uses a heart support structure to transfer energy, in the form of contraction and expansion, from viable heart tissue to less viable or non-viable heart tissue. This structure prevents, compensates for, or treats tissue responses to ischemia, infarction, or other abnormalities.

The embodiments of the invention maintain diastolic compliance of the cardiac tissue and synchronize the expansion and contraction of the diseased tissue to that of viable tissue in order to restore systolic ejection and diastolic filling. This improves wall motion and better restores normal functionality of the heart. As a result, the embodiments of the invention prevent, reduce, and/or delay remodeling of the diseased tissue, decrease the impact of such remodeling on collateral tissue, and preserve all phases of the cardiac cycle.

The embodiments of the invention are also useful in reinforcing abnormal tissue regions to prevent over-expansion of the tissue due to increased afterload and excessive wall tension. As a result, the dyssynchrony, hypokinesis, dyskinesis or akinesis, which occurs when tissue remodels over time, is inhibited. As such, the embodiments of the invention prevent progressive cardiomyopathy and congestive heart failure.

This invention provides electromagnetic assist devices that take advantage of the characteristics of the heart support structure of the invention to impart contraction and expansion throughout the heart, of along a specific region of the ventricles. The electromagnetic assist device strategically induces magnetic fields throughout individual electromagnets coupled to the support structure, which causes an attraction or repulsion of the electromagnets and imparts a contraction or expansion of the heart support structure, and transfers such energy to cardiac tissue.

The present invention also provides enhancements to the overall system to continue to make positioning and securing the heart support structure amenable to less invasive procedures, such an endoscopic, port access approaches. In addition, the present invention enables catheterization approaches to position and secure the heart support structure.

Further features and advantages of the inventions will be elaborated in the detailed description and accompanying drawings.

BRIEF DESCRIPTION OF THE DRAWINGS

FIG. 12A is a perspective view of an anchor used to attach the heart support structure of the present invention to tissue.

FIGS. 12B and 12C show top views of two additional anchor embodiments of the present invention.

FIG. 12D is a side-sectional view of a heart support structure secured to a tissue surface using the anchor embodiments of FIGS. 12A to 12C.

FIG. 14A is a top view of another anchor embodiment.

FIG. 14B is a side-sectional view of a heart support structure secured to a tissue surface using the anchor embodiment of FIG. 14A.

DETAILED DESCRIPTION OF THE INVENTION

Figure 1:
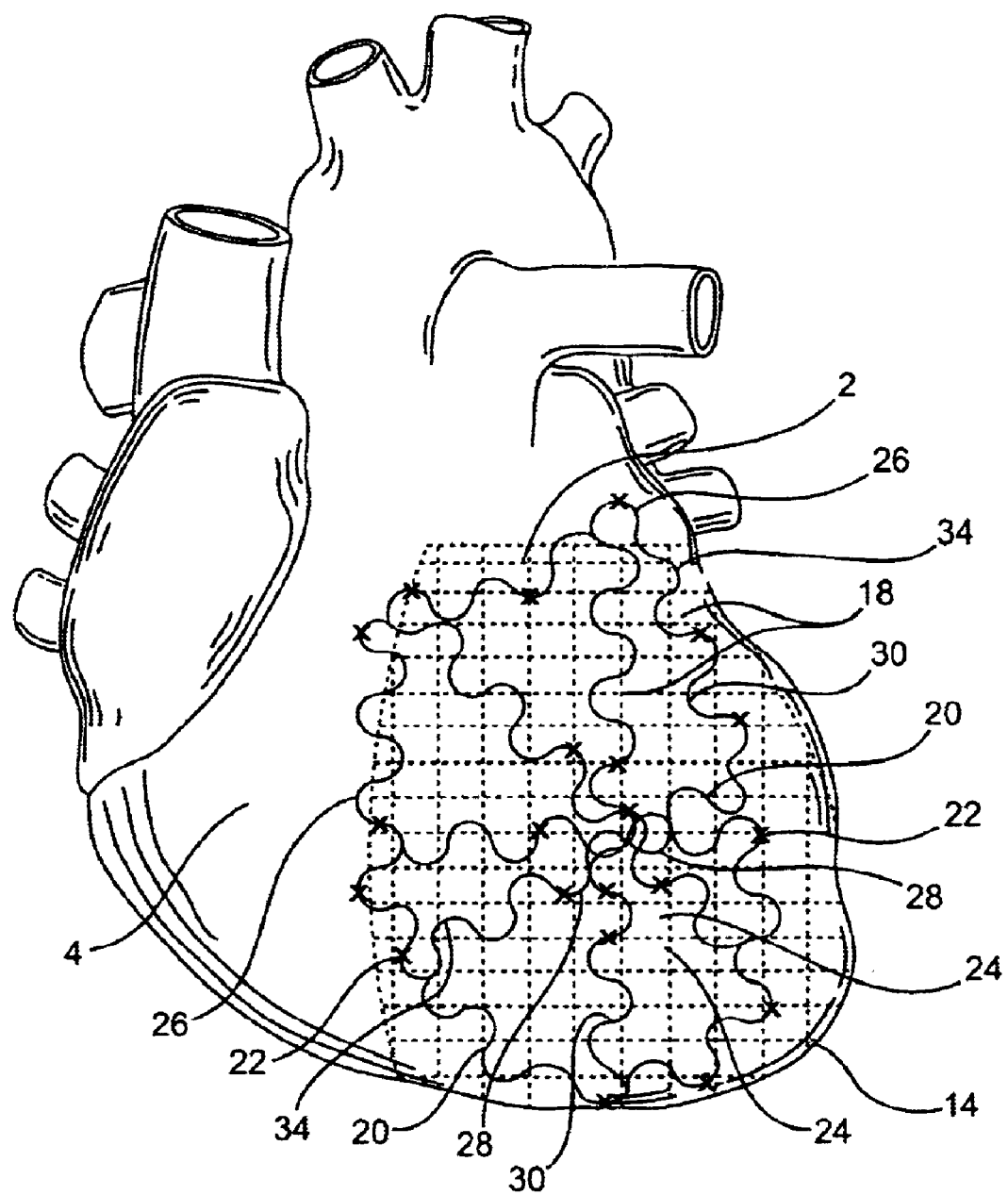
FIG. 1 is a side view of a heart containing a support structure of the present invention attached along an exterior portion of its left ventricle.

The embodiments of the invention are intended to transmit energy from viable tissue regions to less viable or non-viable regions thereby preventing, compensating for, or treating tissue responses to ischemia, infarction, or other abnormalities. Ischemic injury causes tissue remodeling over time and produces dyssynchronous, hypokinetic, dyskinetic or akinetic tissue function. The embodiments of the invention prevent, reduce, and/or delay remodeling of diseased cardiac tissue, and also decrease the impact of such remodeling on collateral tissue. The embodiments of the invention are also useful in reinforcing abnormal tissue regions to prevent over-expansion of the tissue due to increased afterload and excessive wall tension. The embodiments of the invention maintain and/or restore diastolic compliance, wall motion, and ejection fraction to preserve heart functionality. As such, the embodiments of the invention prevent progression of cardiomyopathy and congestive heart failure.

The approach described by this invention, which uses a heart support structure to transfer energy (in the form of artificial contraction and expansion) from viable heart tissue to less viable or non-viable heart tissue, addresses the deficiencies of prior approaches, which purely reduce the end-diastolic diameter of the heart. This invention aids the heart during systolic ejection and diastolic filling to better restore normal functionality of the heart. The heart support structure controls the motion of the heart and synchronizes the contraction and expansion of diseased tissue to that of viable tissue.

The heart support structure also accounts for the natural motion of the heart. As the heart contracts, the cross-sectional diameters of the ventricles decrease and the distance from the mitral valve annulus to the apex of the heart also decreases; as the heart expands, the cross-sectional-diameters of the ventricles increase and the distance from the mitral valve annulus to the apex of the heart also increases. The optimal ratios of expansion (and contraction) between the cross-sectional diameters of the ventricles and the distance from the mitral valve annulus to the apex of the heart may be incorporated in the support structure to further preserve heart functionality. The heart support structure therefore preserves the wall motion and prevents remodeling of the diseased tissue by inhibiting over-expansion and maintaining normal actuation of all phases of the cardiac cycle. As a result, the dyssynchrony, hypokinesis, dyskinesis or akinesis, which occurs when tissue remodels over time, is inhibited.

Heart Support Structures

The heart support structure embodiments consist of one or more components designed to exert force against a diseased (e.g., ischemic or infarcted) region of tissue in response to the contraction or expansion of viable tissue. As such, the support structure transfers energy from viable tissue to less viable or non-viable tissue to control and force movement of injured tissue and prevent remodeling that occurs as a response to ischemic injury.

The heart support structures are preferably fabricated from superelastic (pseudoelastic) shape memory alloys, such as nickel titanium. Superelastic materials elastically deform upon exposure to an external force and return towards their preformed shape upon reduction or removal of the external force. Superelastic shape memory alloys are capable of exhibiting stress-induced martensitic behavior; which means they transform from the preshaped austenitic phase to the softer and more ductile martensite phase upon application of stress and transform back toward the stronger and harder austenite phase once the stress is removed. Superelastic shape memory alloys enable straining the material numerous times without plastically deforming the material. Superelastic shape memory alloys are also light in weight, biocompatible, and exhibit excellent tensile strengths such that they may be attached to the heart without substantially adding weight or bulk.

The characteristics of superelastic shape memory alloys described above highlight their utility in providing a support structure for the heart because they withstand continuous and frequent deflections without plastically deforming or observing fatigue failures. Superelastic support structures may also be elastically deflected into small radii of curvature and return towards their preformed configuration once the external force causing the deflection is removed. Although other, more conventional materials such as stainless steel may be used in this application, their geometry is likely to be less fine or compact because their material properties dictate that the total elastic energy stored in a given device is much lower. Other known metal, alloy, and thermoplastic materials plastically deform when deflected into similar radii of curvature, using comparable strains, and are unable to return towards their original configuration. As such, superelastic support structures permit deflections into smaller radii of curvature than other metals, alloys, and polymers resulting in the ability to withstand larger strains without failing; they are also capable of exerting substantial force when deflected.

We prefer that support structures fabricated from shape memory alloys (e.g., nickel titanium) be engineered to form stress-induced martensite (SIM) at body temperature. The composition of the shape memory alloy is preferably chosen to produce martensitic transformation temperatures ($M_s$ and $M_f$) and austenitic transformation temperatures ($A_s$ and $A_f$) such that the alloy exhibits stress induced martensite up to a temperature $M_d$, greater than $A_f$.

The relative composition of nickel and titanium determines the $A_f$ of the shape memory allow. For example, nickel titanium having an atomic ratio of 51.2% Ni and 48.8% Ti exhibits an $A_f$ of approximately −20 C; nickel titanium having an atomic ratio of 50% Ni to 50% Ti exhibits an $A_f$ of approximately 100 C (Melzer A, Pelton A. "Superelastic Shape-Memory Technology of Nitinol in Medicine" *Min Invas Ther & Allied Technot* 2000: 9(2) 59–60).

Preferably the composition and fabrication of the nickel titanium is chosen such that the $A_f$ is below 32 C. Such materials are able to withstand strains as high as 10% without plastically deforming. As such, these superelastic materials are capable of elastically exerting force upon deflection.

Superelastic shape memory alloys that do not exhibit stress-induced martensitic behavior at body temperature but enable elastic deformation through the range of motion the material is exposed may alternatively be used. Materials other than superelastic shape memory alloys may be used for the support structures provided they can be elastically deformed within the temperature, stress, and strain parameters required to maximize the elastic restoring force. Such materials include other shape memory alloys, spring stainless steel 17-7, ELGILOY (Elgiloy LP, Elgin, IL), superelastic polymers, etc.

Throughout this description, discussions of external force preferably refer to the contraction and/or expansion of viable tissue causing the support structure to respond accordingly unless otherwise specified. Alternatively, another external means, artificial, biological, or a combination of artificial and biocompatible means for compressing and/or expanding the support structure may be used as will be discussed later.

Other materials may be used as a covering to the support structure, including thermoplastics (e.g., polytetrafluoroethylene or PTFE), thermoset plastics (e.g., polyethylene terephthalate, polyester), or silicone. For example, heart support structures fabricated from nickel titanium may be covered with expanded PTFE by sintering layers of expanded PTFE positioned to encompass the support structure material. Alternatively, the support structures may be coated with silicone, which when allowed to cure produces a covering over the support structure.

The heart support structure may be coated with materials such as parylene or other hydrophilic substrates that are biologically inert and reduce the surface friction. To further reduce the surface friction, metallic or metallic alloy fittings may be electropolished. Evidence suggests that electropolishing reduces adhesion because of the smooth surface and low surface tension. Alternatively, the heart support structures may be coated with heparin, thromboresistance substances (e.g., glycoprotein IIb/IIIa inhibitors), antiproliferative substances (e.g., Rapamycin), or other coatings designed to prevent adhesion, thrombosis for blood contacting support structures, hyperplasia, or other tissue response that may adversely impact the functionality of the heart support structure. Alternatively, materials such as platinum, gold, tantalum, tin, tin-indium, zirconium, zirconium alloy, zirconium oxide, zirconium nitrate, phosphatidyl-choline, pyrolytic carbon, or others may be deposited onto the heart support structure surface using electroplating, sputtering vacuum evaporation, ion assisted beam deposition, vapor deposition, silver doping, boronation techniques, a salt bath, or other coating process.

A still further improvement of the heart support structure that is within the scope of the present invention is to include beta or gamma radiation sources on the heart support structure. A beta or gamma source isotope having an average half-life of approximately 15 days such as Phosphorous 32 or Palladium 103 may be placed on the heart support structure using an ion-implantation process, chemical adhesion process, or other suitable method.

The heart support structure embodiments may be fabricated from a sheet of material cut into the desired pattern and formed (e.g., through a heat treatment process) into the desired geometry (planar, conical, elliptical, cylindrical, or other shape). To produce these heart support structures, the raw material may be fabricated into the desired pattern by chemical etching, electron discharge machining (EDM), laser cutting, or other manufacturing process. Heart support structures fabricated from sheet stock are then wrapped or otherwise placed around mandrels having the desired resting three-dimensional profile(s) and the heart support structure is heated until it assumes this configuration. After heating, the support structure is quenched or otherwise allowed to return to room temperature, at which the support structure maintains the preformed shape. If any sides are to be bonded, spot welding, laser welding, or other manufacturing process may be employed.

Alternatively, heart support structure embodiments of the present invention may be fabricated from a tube of material having a desired cross-sectional geometry. The desired pattern of links, anchors, anchor pins, holes, slots, and/or cells may be fabricated on the tubular metal material and may be created using chemical etching, EDM, laser cutting, or other manufacturing process. These heart support structures may be thermally formed into the desired planar or three-dimensional profile depending on the desired shape of the heart support structure.

FIG. 1 shows a heart containing a support structure 20 secured to the epicardial surface at specific attachment points 22 along a section of the left ventricle (LV) 2. A tissue interface 18 may or may not be positioned between support structure 20 and the epicardium, as will be discussed below. In this particular embodiment, peripheral links 26 extend around the injured tissue 24 (e.g., ischemic or infarcted). Support links 30 extend from peripheral links 26 into the injured tissue 24 to provide the structure from which contraction and/or expansion energy may be transferred from peripheral links 26 to a central region 28 of the support structure located throughout the injured tissue 24. The geometry of support structure 20 depends on the location of the injured tissue. If the injured tissue 24 is on the left ventricular free wall, support structure 20 may be planar or have a slightly curved three-dimensional profile. If the injured tissue 24 is apical, support structure 20 may be generally conical or approximate one half of an ellipsoid.

The support structure embodiment in FIG. 1 is secured to the left ventricle at desired locations throughout a central region 28 within the injured tissue 24, and along peripheral links 26 and/or support links 30. Central region 28 of the support structure may be a discrete point or a two-dimensional surface, or it may constitute a region of multiple intersecting, interlocking, or adjacent support links 30. Central region 28 shown in FIG. 1 consists of four intersecting support links 30; we prefer that a minimum of two intersecting support links 30 be used for this configuration.

Each support link 30 extends from at least one peripheral link 26 located past one end of the injured tissue 24, and attached to viable tissue, to at least one peripheral link 26 located past the opposite end of the injured tissue 24, and attached to viable tissue. An alternative configuration involves individual support links that terminate at the central region 28 and are not attached to the other independent support links throughout the central region 28 or using peripheral links.

Peripheral links 26 and support links 30 in the embodiment of FIG. 1 are designed for different purposes. Support links 30 are designed to cause corresponding movement of the injured tissue 24 in response to contraction or expansion of the viable tissue to which support links 30 are secured. As such, the support links require sufficient axial stiffness to contract or expand the injured tissue 24 in response to movement of the proximal ends of the support links located along peripheral links 26 of support structure 20. Support links 30 must also have sufficient flexibility so that they do not hinder movement of viable tissue between central region 28 and peripheral links 26 of the support structure. Peripheral links 26 must be flexible so to be able to move coincident with contraction and expansion of the left ventricle, and durable enough to maintain the integrity of heart support structure 20 despite continued movement of the support structure.

Figure 2:
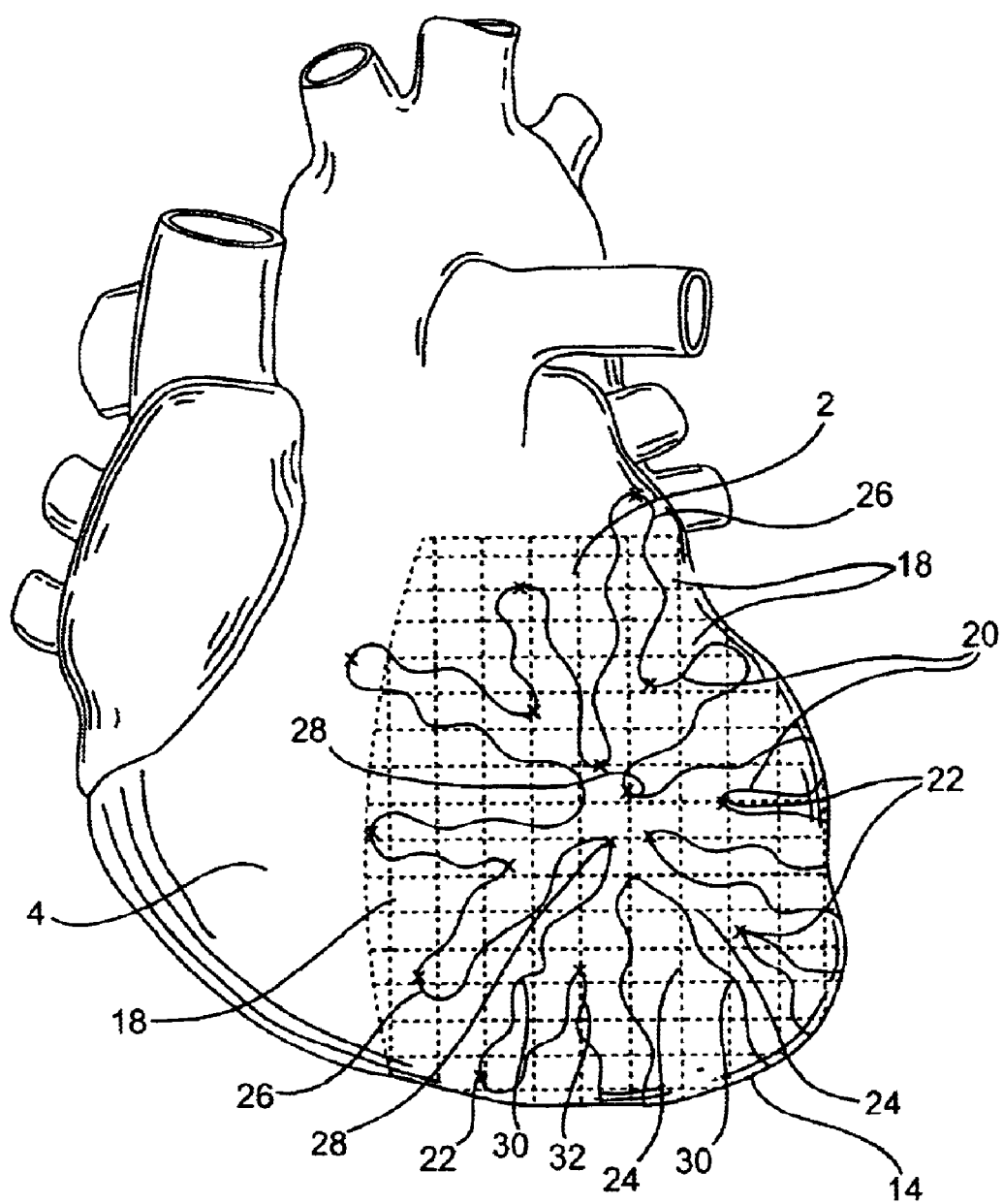
FIG. 2 is a side view of a heart containing another support structure of the present invention attached along an exterior portion of its left ventricle.

FIG. 2 shows a heart containing another support structure embodiment 20 emanating from a central region 28, located within injured tissue 24. The peripheral links 26 for this embodiment do not extend completely around the injured tissue, but connect adjacent support links 30 at their proximal ends and are attached to viable tissue. Support links 30 interconnect in central region 28 and the unions are secured to the injured tissue 24 at attachment points 22. Support links 30 in this embodiment also interconnect along a middle section 32 located between central region 28 and the periphery of the support structure. Middle section 32 unions are also secured to the tissue surface at attachment points 22.

It should be noted that middle section 32 may be located along central region 28, anywhere between central region 28 and peripheral links 26, and/or along the proximal end of the support structure defined by peripheral links 26. Different middle sections 32 may be positioned at different locations along the tissue surface, depending on the axial stiffness and flexibility requirements of support links 30.

Figure 3:
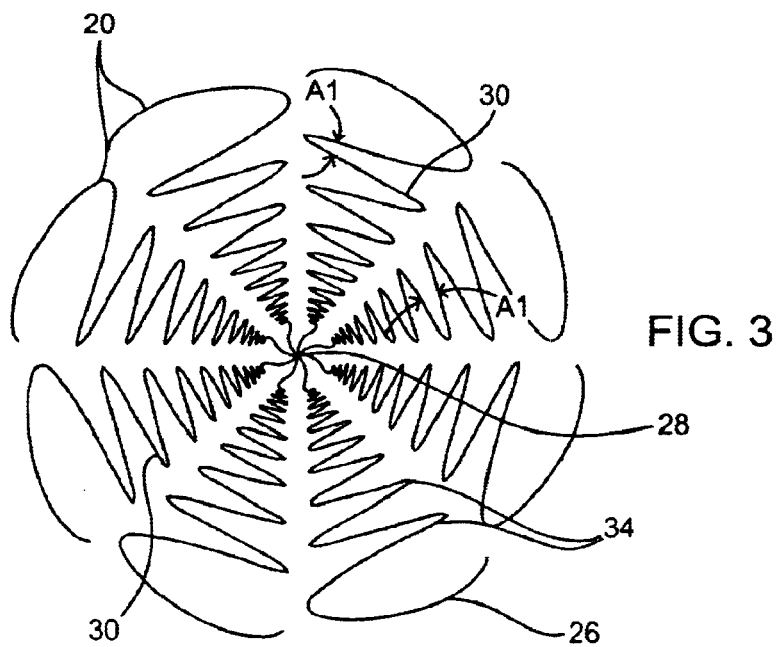
FIG. 3 is a flattened view of a heart support structure of the present invention.
Figure 4:
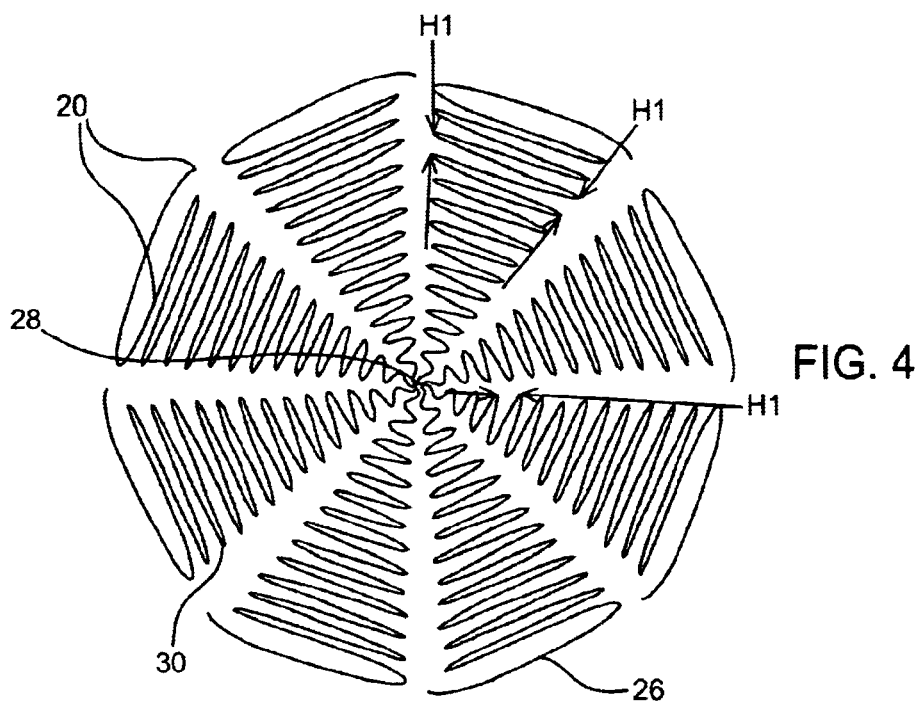
FIG. 4 is a flattened view of another heart support structure of the present invention.

FIGS. 3 and 4 show flattened profiles of two alternative support structures of the present invention. Support structures 20 incorporate eight support links 30 that extend from a central point 28 and snake towards peripheral links 26; a minimum of two support links 30 are used to form this support structure embodiment. Each turn of a snaking support link 30 defines a node 34. The relation of the support links to the nodes defines the stiffness profile of support structure 20. In FIG. 3, support nodes 34 are separated such that the angle A1 between adjacent turns of each snaking support link 30 is constant. In FIG. 4, the distance H1 between adjacent support nodes 34 is constant.

The parameters of each support link 30 (width, wall thickness, total length, and turn length) also influence the stiffness. The stiffness profile of the support structure determines the degree of contraction and expansion transferred from viable tissue to injured tissue 24 throughout the support structure 20. This profile may be optimized depending on the anticipated position of various support links 30 relative to anatomic structures and desired responses.

For example, the apex of the heart contracts and expands at a different degree than the left ventricular free wall; the right ventricle (RV) is much more compliant than the left ventricle. As such, support structure 20 must incorporate such profiles to maximize the restoration of systolic ejection and diastolic filling. More than one target zone of injured tissue may be addressed with a single support structure or multiple support structures by tailoring the stiffness profile(s) of the support structure(s) to ensure the desired contraction and expansion force is transferred and distributed throughout the surface of the targeted tissue surface.

Figure 5:
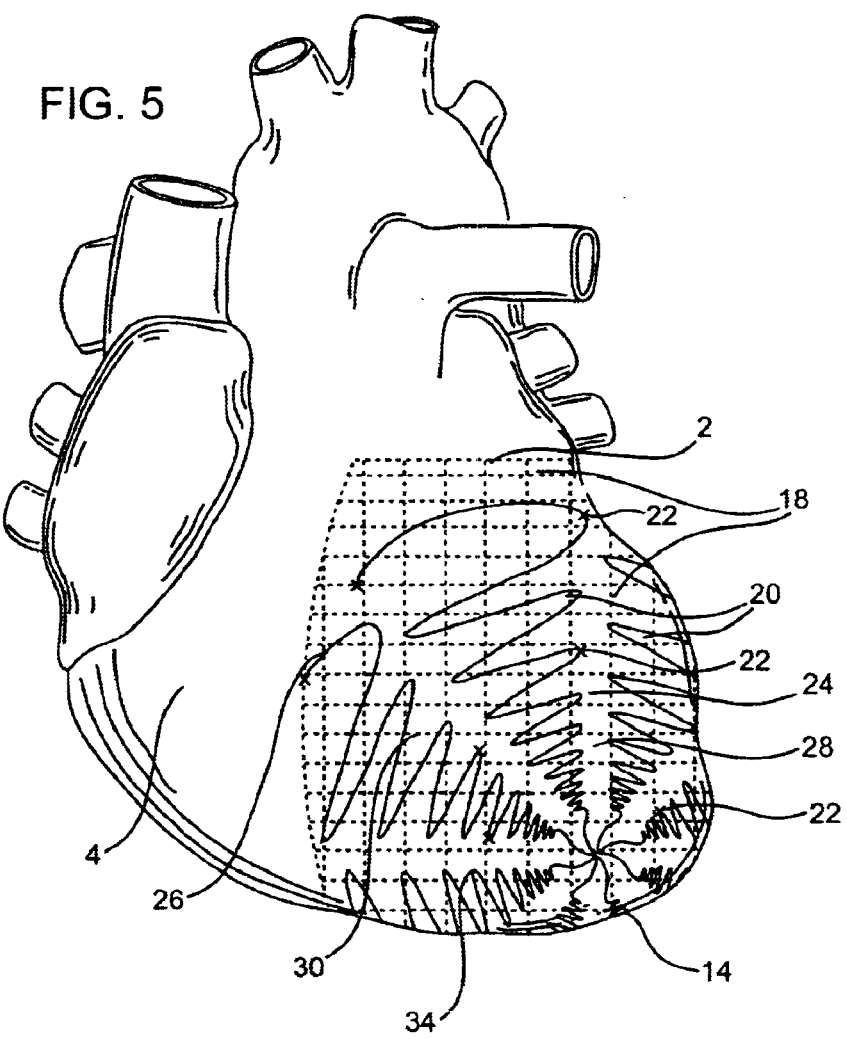
FIG. 5 is a side view of a heart containing the support structure of FIG. 4 emanating from the apex of the heart.

FIG. 5 shows the support structure shown in FIG. 4 thermally formed into a conical geometry and positioned such that central region 28 (in this case a point) is located at the apex 14 of the heart. As will be discusses later, a tissue interface is positioned between support structure 20 and the tissue surface. This support structure 20 is secured to the tissue surface at attachment points 22 in central region 28, interspersed throughout nodes 34 along support links 30, and along peripheral links 26. This support structure embodiment is configured to treat apical infarcts or ischemic regions and/or cover both ventricles. As previously discussed, discrete support links 30 may be fabricated with various parameters (width, wall thickness, length), node separation (H1), or turn length to impart different stiffness profiles throughout the heart.

For example, support links 30 positioned along the right ventricle 4 require substantially less stiffness than those positioned along the left ventricle 2 to impart the same amount of contraction and expansion in the right and left ventricle respectively. In addition, the amount of contraction and expansion for the right ventricle differs from that for the left ventricle, thus the stiffness profile of apically positioned support structures must account for the disparity.

Figure 6:
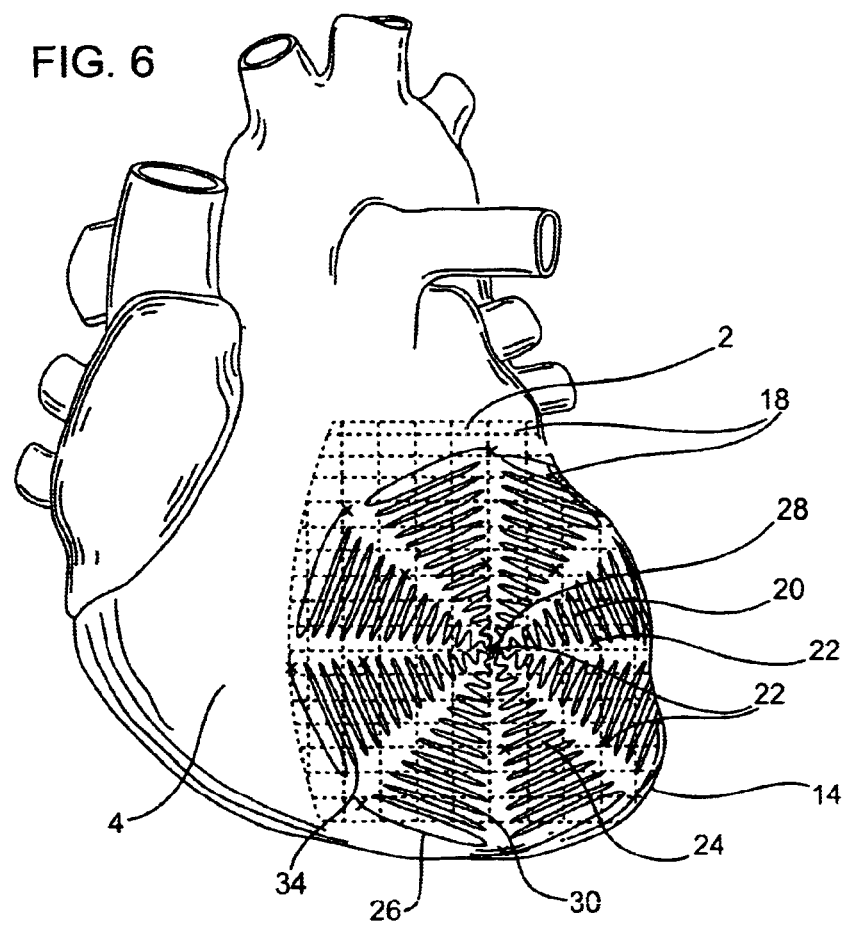
FIG. 6 is a side view of a heart containing the support structure of FIG. 4 emanating from the ischemic or infracted region of the heart.

FIG. 6 shows the support structure of FIG. 4 emanating from a central region 28 positioned within injured tissue 24 located along the left ventricular free wall. Support links 30 extend from a point at central region 28 and extend to peripheral links 26 positioned at a desired distance beyond the injured tissue 24. This particular support structure is configured to isolate the transfer of contraction and expansion energy from viable tissue, residing outside a border zone of injured tissue 24, to injured tissue 24.

Figure 7:
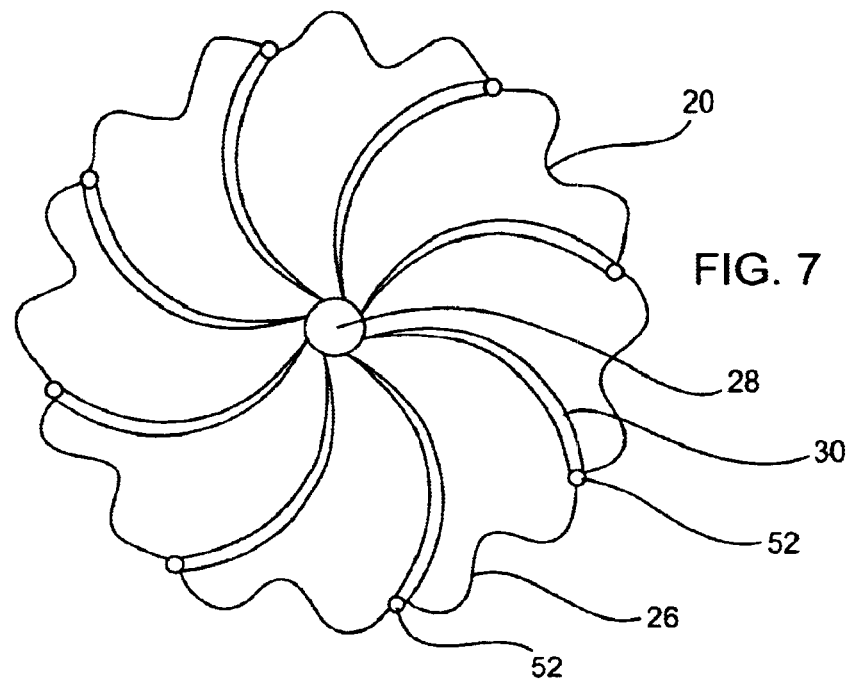
FIG. 7 is a flattened view of yet another heart support structure of the present invention.

FIG. 7 shows an alternative support structure embodiment that interconnects support links 30 around a circle or other shape used to define central zone 28. Support links 30 are tapered from peripheral links 26 to central zone 28. Support links 30 may be tapered in width (as shown in FIG. 7), wall thickness, and/or other parameters capable of influencing the structure's axial stiffness and flexibility along the length of support link.

As previously stated, individual support links 30 may incorporate different stiffness characteristics to tailor the stiffness profile of the support structure to the physiologic requirements. The proximal ends of the support links 30 are attached to the peripheral links 26 such that the intersection forms anchors 52 or defines an attachment point. Peripheral links 26 are configured significantly more flexible than support links 30 since peripheral links 26 maintain the integrity of support structure 20 but do not transfer energy throughout tissue encompassed by the support structure.

Figure 8:
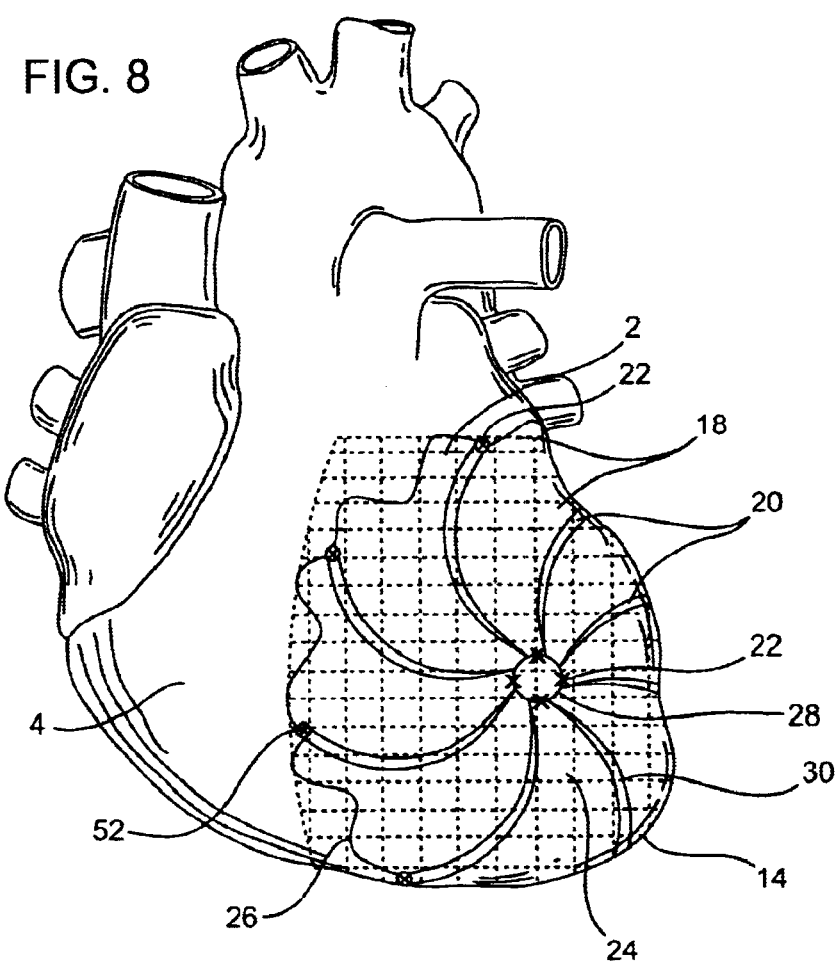
FIG. 8 is a side view of a heart containing the support structure of FIG. 7 emanating from the ischemic or infracted region of the heart.

FIG. 8 shows a heart that contains the support structure embodiment of FIG. 7. Central zone 28 is located along the injured tissue region 24. The individual peripheral links 26 extend completely around the injured tissue region 24 at distances defined by the individual support links 30. These distances may be constant or may vary by changing the length and/or shape of each support link 30. The distances between peripheral links 26 and central zone 28 also impact the stiffness profile of the support structure and influence the transfer of contraction and expansion energy from viable tissue to the injured tissue zone 24.

The central zones of the various support structure embodiments discussed above may be integral to support links 30 or alternatively may be comprised of one or more separate components that are attached to the support links. This separate component(s) may be fabricated from the same material as the support links or a different material. For instance, compliant materials such as silicone, urethane, or other biological materials having high percent elongation characteristics may be used.

Figure 9B:
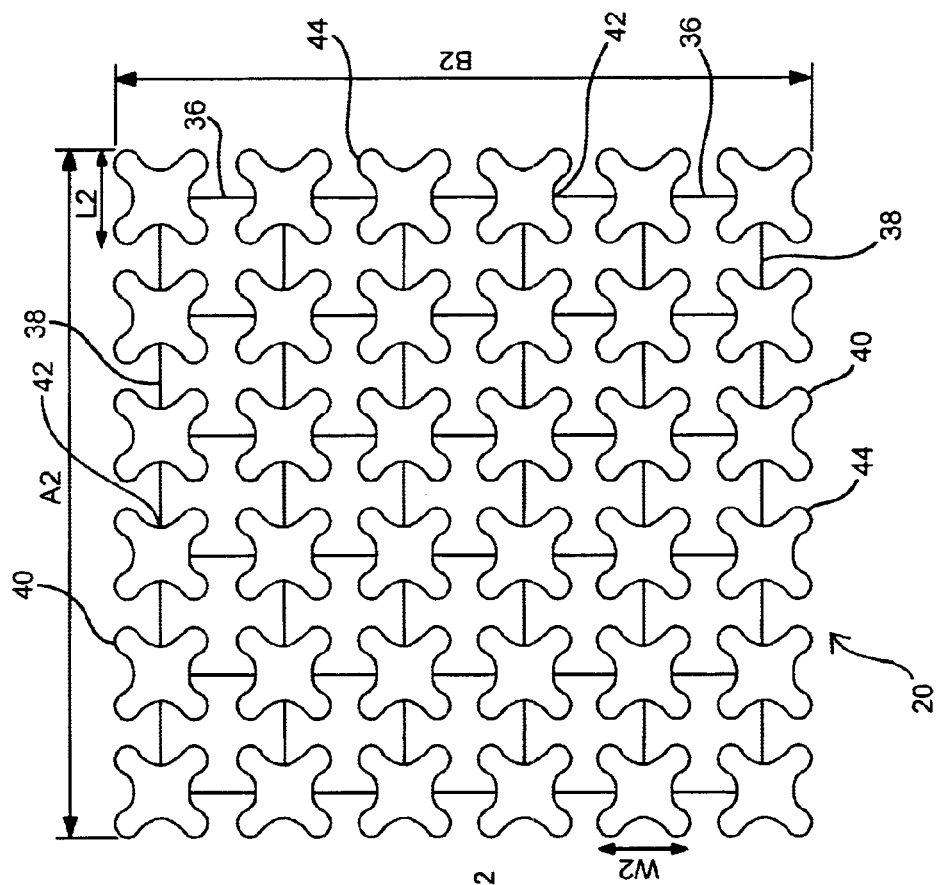
FIG. 9B is a flattened view of the heart support structure of FIG. 9A in its expanded state.
Figure 9A:
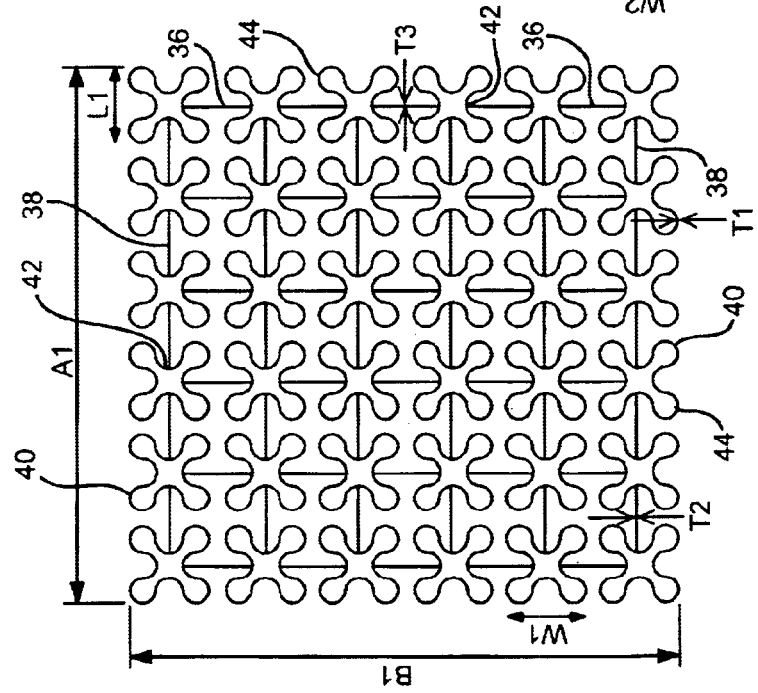
FIG. 9A is a flattened view of still another heart support structure of the present invention in its compressed state.

FIGS. 9A and 9B show an alternative support structure embodiment that causes the width to expand as the length expands (or vice versa) and causes the width to contract as the length contracts (or vice versa). For example, as an external force causes the length of the support structure to expand from position A1 to position A2, the width of the support structure expands from position B1 to position B2. The external force described in this embodiment may be, for example, movement of viable tissue. The expansion or contraction energy is transferred from the actuated section of the support structure throughout the remainder of the support structure causing cardiac tissue, to which the support structure is attached, to expand or contract accordingly.

The characteristics of this support structure are substantially different than the flattened profile of any prior stent or stent-graft. Conventional stents or stent-grafts contract or minimally change in length as the diameter is expanded. Stents or stent-grafts fabricated with the support structure geometry shown in FIGS. 9A and 9B expand in length as the diameter is expanded. As such the support structure embodiment in FIGS. 9A and 9B may be fabricated as a complete tube and used as a stent or stent-graft (if the support structure is attached to at least one end of graft material).

The support structure embodiment shown in FIGS. 9A and 9B incorporates cells 40 interconnected by horizontal links 38 and vertical links 36 that are attached to the cells at nodes 42. The cells also incorporate hinges 44 to permit expansion and contraction of the cells 40 in response to an external force. As the width (or length) of each cell expands from W1 to W2 (or L1 to L2), cell nodes 42 located at vertical links 36 and horizontal links 38 are deflected outward, about hinges 44, thereby causing the length (or width) of the cell to also expand from L1 to L2 (or W1 to W2). This transfers the expansion force to adjacent cells, thereby propagating the expansion throughout the support structure. The converse is also true: as the width (or length) of each cell contracts from W2 to W1 (or L2 to L1), the nodes are deflected inward, causing the length (or width) of the cell to also contract from L2 to L 1 (or W2 to W1) and transferring the contraction force to adjacent cells.

The support structure embodiment of FIGS. 9A and 9B is shown as having arrays of cells positioned equidistant along its the width and length, where each cell has a constant width and length in the relaxed position. Alternatively, the cells may be positioned such that vertical links 36 and horizontal links 38 are generally not perpendicular. As such, the length L1 (or width W1) of each cell may be decreased along the width B1 (or length A1) of the support structure to produce a taper along the width (or length) of the support structure.

Other combinations of cell widths W1 and lengths L1 may be used to tailor the stiffness and degree of ratio of expansion between the width and length for the support structure to the geometry of the heart and the amount of expansion and contraction desired throughout the support structure.

For example, to tailor this support structure embodiment so it may be positioned apically, length A 1 of the support structure may be tapered along width B 1 such that the length of each cell L1 decreases at specified intervals and/or the length of each horizontal link 38 decreases. Such modifications potentially impact the stiffness profile of the support structure; therefore, cell width T1, horizontal link width T2, vertical link width T3, and/or wall thickness of each cell and link may be decreased as the cells are tapered so as to compensate for the increase in stiffness associated with decreasing the cell dimensions.

Cell width T1, horizontal link width T2, vertical link width T3, and/or wall thickness of each cell and link may alternatively be varied to predefine the stiffness profile of the support structure, accommodate nonlinear expansion or contraction requirements throughout the ventricles, or address anatomic variances that warrant changes in support structure geometry or stiffness.

Figure 10:
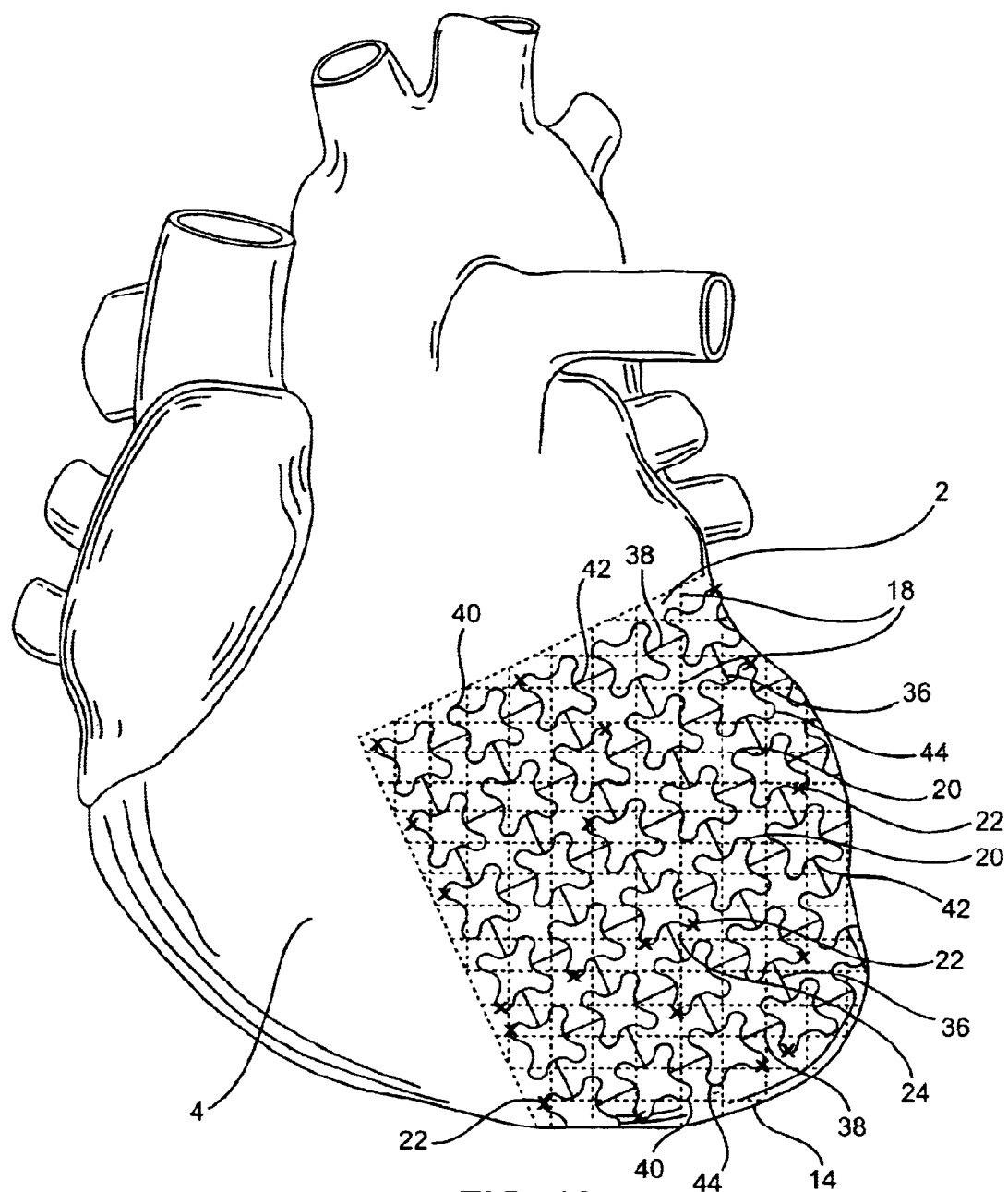
FIG. 10 is a side view of a heart containing the support structure of FIG. 9B.

FIG. 10 shows a heart with the support structure embodiment of FIG. 9B attached to the left ventricle. Support structure 20 is centered around the injured tissue region 24 to optimally transfer the expansion and contraction forces from viable tissue to the injured tissue 24. The support structure embodiment of FIG. 10 is shown in the enlarged configuration, reflecting the end-diastolic orientation and geometry of the support structure.

Positioning and securing support structure 20 to the surface of the heart chamber is preferably performed with the heart at end-diastole and with the support structure in the enlarged orientation (either by preshaping or manually stressing). In certain scenarios, the support structure may be configured to exert some contractile force throughout the cardiac cycle, even during end-diastole. To accomplish this, the support structure is positioned and secured to the tissue surface during end-diastole with the support structure stressed into its expanded orientation. Securing the support structure to the heart during end-diastole ensures better seating against the ventricle and the observed spacing between attachment points 22 ensures optimal transfer of contraction and expansion energy from the support link attachment points to the injured tissue 24.

It should be noted that the steps of positioning and securing support structure 20 to the tissue surface may alternatively be performed at end-systole with support structure 20 in the contracted orientation, or at any phase in the cardiac cycle. It should also be noted that the positioning and design of the support structure may bias the structure such that a continuous contractile force exerted by the elasticity of the support structure is applied even during end-diastole, a continuous expansion force is applied even during end-systole, or a contractile force is applied during relaxation and diastolic filling and an expansion force is applied during contraction and systolic ejection.

Figure 11:
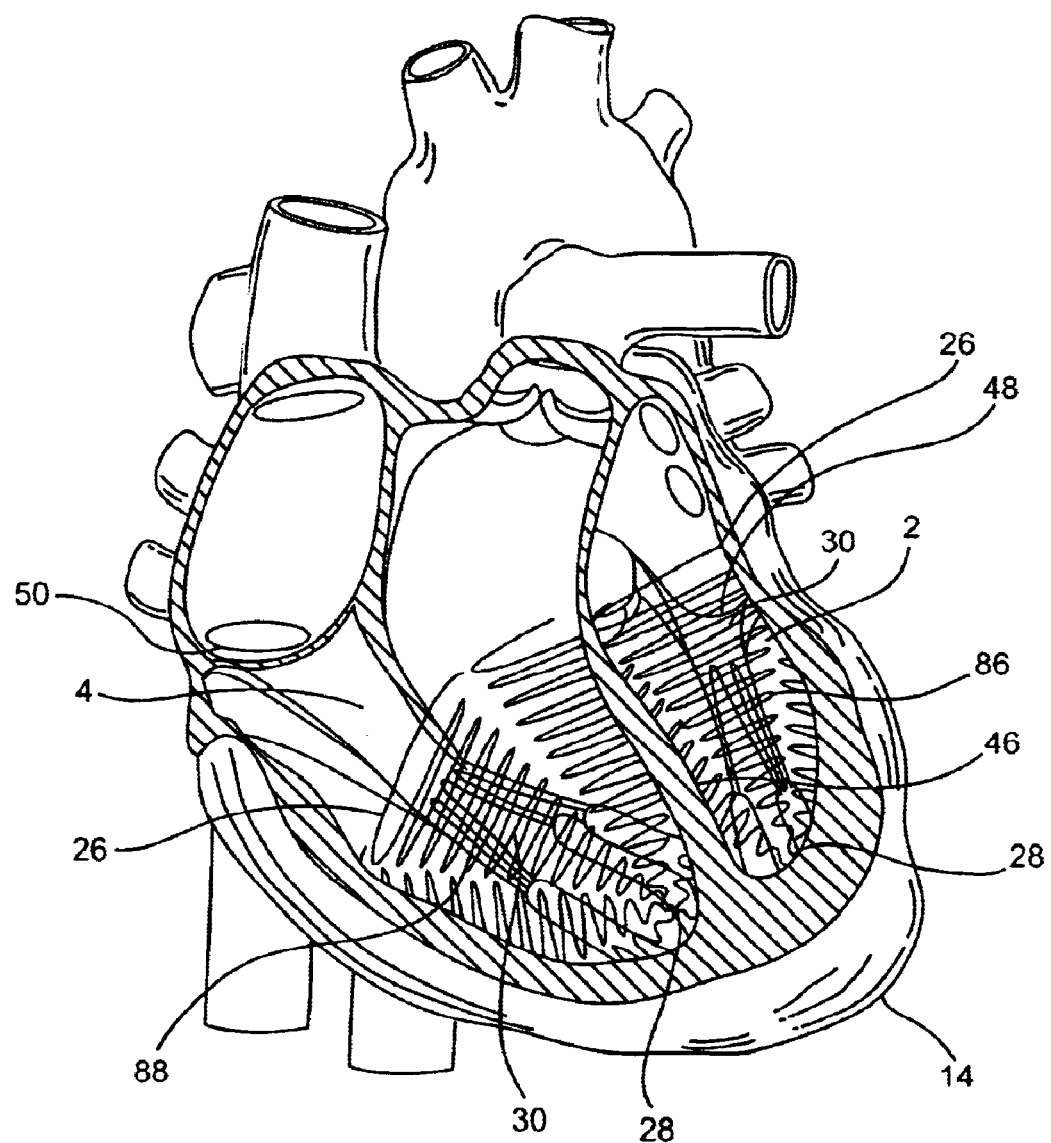
FIG. 11 is a side-sectional view of a heart containing support structures of the present invention along the interior surface of the left ventricle and right ventricle.

The embodiments described above show the support structure attached to the epicardial surface of the ventricles. Alternatively, as shown in FIG. 11, at least one support structure 86 and/or 88 may be secured to the endocardial surface of at least one of the left ventricle 2 and the right ventricle 4. Any of the support structure embodiments described above may be modified to enable positioning the support structure against the endocardial surface. For purposes of discussion, the embodiment of FIG. 4 is shown as the left ventricular support structure 86 and the right ventricular support structure 88 in FIG. 11. The support structures 86 and 88 are configured such that the central regions 28 of each is located at the apex 14 of the left ventricle 2 and right ventricle 4.

The LV support structure 86 is preferably preshaped to match the end-diastolic geometry and optimal size of the left ventricular cavity. Peripheral links 26 and support links 30 of LV support structure 86 do not interfere with the operation of mitral valve 48, the papillary muscles, or the chordae tendonae. Support links 30 may be fabricated with spaces where the papillary muscles extend into the left ventricular cavity and where the chordae tendonae extend from the papillary muscles and connect to mitral valve 48. Support links 30 are distributed throughout the endocardial surface of the left ventricle extending from the interventricular septum 46 completely around the left ventricular free wall. As such, injured tissue regions extending into or located along the interventricular septum may be covered by support structure 86. Alternatively, the left ventricular support structure 86 may be designed to cover only the interventricular septum, the left ventricular free wall, or other endocardial tissue region.

The RV support structure 88 is preferably preshaped to match the end-diastolic geometry and optimal size of the right ventricular cavity. Peripheral links 26 and support links 30 of RV support structure 88 do not interfere with the operation of the tricuspid valve 50, the papillary muscles, or the chordae tendonae. Support links 30 may be fabricated with spaces where the papillary muscles extend into the right ventricular cavity and where the chordae tendonae extend from the papillary muscles and connect to the tricuspid valve 50. Support links 30 are distributed throughout the endocardial surface of the right ventricle extending from the interventricular septum 46 completely around the right ventricular free wall. As such, injured tissue regions extending into or located along the interventricular septum may be covered by the support structure 86. Alternatively, the right ventricular support structure 86 may be designed to cover only the interventricular septum, the right ventricular free wall, or other endocardial tissue region. For injured tissue isolated within the interventricular septum, the right ventricle is the preferred location to position and secure a support structure against the endocardial surface in which the support structure is designed to solely cause expansion and contraction of injured tissue along the interventricular septum.

Support structures located along the endocardial surface of the right and/or left ventricle may be combined with support structures located along the epicardial surface to enhance the transfer of energy from viable tissue to less viable or non-viable tissue, especially when several injured tissue regions are dispersed throughout the heart. The support structures may be independent such that the endocardial support structures are not attached to the epicardial support structures. Alternatively, individual support links of the endocardial support structures may be inserted through the myocardium and may be connected to epicardial support structures so as to interconnect the expansion and contraction of the endocardial support structures to the epicardial support structures. This is especially relevant when the injured tissue extends from the interventricular septum to the left ventricular free wall and the desired position of the support structure extends from the right ventricular endocardial surface of the interventricular septum through the myocardium of the right ventricle and along the epicardial surface of the left ventricle. Other combinations of endocardially and epicardially positioned support structures may be used to address other indications or injured tissue locations.

The various support structure embodiments described above exhibit isotropic, orthotropic, or anisotropic structural properties. It should be noted that the embodiments of the invention may be modified to exhibit different structural properties (isotropic, orthotropic, or anisotropic) to match the inherent structural properties of the tissue surface to which the support structure encompasses, or to tailor the support structure to specific tissue surface locations. They may also be configured to modify the structural properties of the tissue surface to reduce wall tension, improve contractility, or otherwise change the functionality of the heart. It should also be noted that the structural properties of the support structures described above may be modified to address other applications as are known to those of skill in the art.

Support Structure Anchoring

The heart support structures described above typically are secured to the epicardial surface and/or endocardial surface at attachment points 22. A variety of bonding methodologies may be employed including adhesives (fibrinogen, etc.), coagulating the surface to the support structure by heating the tissue, or mechanically anchoring the support structure to the tissue surface, a technique that is discussed below. The support structures may incorporate anchors that penetrate into tissue, holes to pass suture, flaps that become entangled in the trabecula of the ventricles for endocardial support structures, or other mechanical securing mechanism with which to attach the heart support structure to the tissue surface. The heart support structure is alternatively secured to the tissue surface using commercially available implantable clips, staples, or other means.

FIG. 12A shows a support structure 20 that incorporates an anchor 52 designed to penetrate into tissue. Anchor pins 54 extend radially away from anchor 52 at acute angles to maintain the position of the anchor within the tissue surface, once positioned. Anchor pins 54 may extend from the anchor in curves as shown in FIG. 12B, along lines as shown in FIG. 12C, or in other orientations. As shown in FIG. 12D, support structure 20 is secure to the tissue surface after anchor 52 is inserted through the first heart surface (epicardium 60 or endocardium 58) and anchor pins 54 are constrained from axial movement by the myocardium 56.

Alternatively, the anchor may be inserted past the first heart surface (epicardium 60 or endocardium 58), through the myocardium 56, and past the second heart surface (endocardium 58 or epicardium 60) such that the anchor pins are constrained by the second heart surface. As shown in FIG. 12D, a tissue interface 18 spaces the support structure from the tissue surface, as will be described in detail below; even so, tissue interface 18 must enable insertion of the anchor during positioning and securing of the support structure.

During deployment, anchor pins 54 may be constrained with a delivery tube or may be allowed to deflect into a reduced diameter as the anchor is inserted through the tissue surface (and tissue interface 18, if any). The outward bias of anchor pins 54 causes them to extend radially once positioned within the myocardium and prevent pulling the anchor away from the tissue surface. The anchor shown in FIGS. 12A to d may be fabricated from as a separate component that is bonded (e.g., spot welding, soldering, adhesive bonding, or other suitable attachment means) to the links of the support structure at predefined locations. Alternatively, the anchor may be cut (e.g., laser cutting, EDM, chemical etching, water jet cutting, or other suitable process) from links in the support structure and thermally formed into the desired anchor and anchor pin shapes.

Figure 13A:
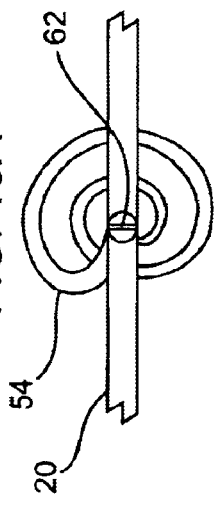
FIG. 13A is a top view of another anchor embodiment.
Figure 13B:
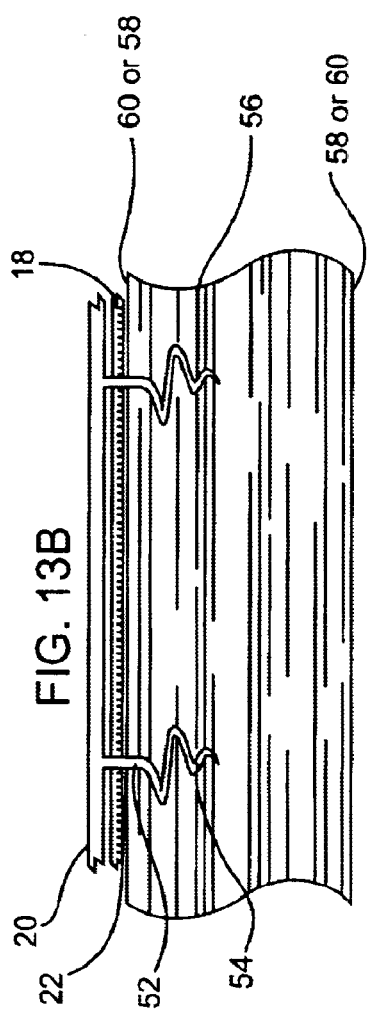
FIG. 13B is a side-sectional view of a heart support structure secured to a tissue surface using the anchor embodiment of FIG. 13A.
Figure 13C:
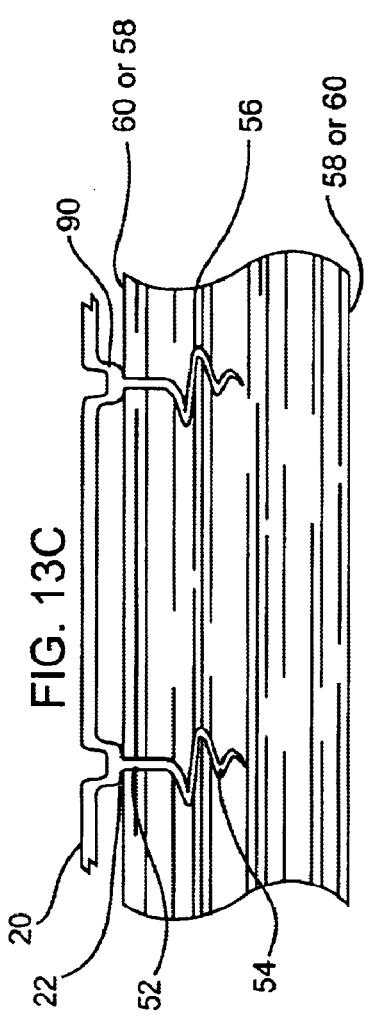
FIG. 13C is a side-sectional view of a heart support structure secured to a tissue surface using an alternative anchor embodiment.

FIGS. 13A to 13C show an alternative anchor 52 embodiment. This anchor 52 shapes anchor pin 54 into a screw configuration such that the anchor is inserted through the tissue surface 60 or 58 (and the tissue interface 18, if any) as the anchor is rotated. This anchor 52 may be a separate component that is independently rotatable relative to the links of support structure 20, as shown in FIG. 13A. As such, a screw head 62 may be formed in the proximal end of the anchor and used to rotate the anchor relative to the links of the support structure 20. Alternatively, the anchor pin may be integral to the links of support structure 20 and are straightened in a delivery tube for insertion through the tissue surface 60 or 58 (and the tissue interface 18, if any). The delivery tube is removed from around the anchor pin, allowing the anchor pin to return towards its preformed shape once positioned in the myocardium 56.

The anchor pin of these embodiments may be configured with alternative geometries to facilitate deployment and/or attachment of the support structure to the tissue surface. For example, a single anchor pin may extend from the anchor as a hook which is capable of being inserted through the tissue surface by angling the anchor pin such that the distal tip penetrates through the tissue surface and advancing the rest of the anchor.

The anchors described previously may also be connected to an electrosurgical generator capable of transmitting radio frequency (RF) energy to tissue contacting the anchors. As such, tissue adjacent the anchors resistively heats in response to exposure to the RF energy, causing the tissue to coagulate to the anchors and enhance the bond between the anchors (and thus the support structure) and the tissue surface.

As shown in FIGS. 14A and 14B, holes 64 may be incorporated in the links of support structure 20 such that commercially available suture 66 (alternatively, clips or staples) may be inserted through one hole 64, past the tissue surface 60 or 58, partially through the myocardium 56, back through the tissue surface 60 or 58, and back through the second hole 64. Once positioned, suture 66 is tied thereby securing the link of the support structure to the tissue surface. Alternatively, suture 66 may be inserted through only one of the holes 64, or the suture 66 may be passed around the width of a support structure link where no holes are required.

Tissue Interface

As shown in FIGS. 12D, 13B, and 14B, tissue interface 18 spaces support structure 20 from the surface of the heart (60 or 58), and inhibits abrading the surface of the heart due to components of the support structure moving along the surface of the heart. Tissue interface 18 may be a synthetic graft material, harvested biological material, or other lubricious structure.

Alternatively, tissue interface 18 may be a spacer 90 incorporated in support structure 20 at attachment point 22 to maintain separation between the epicardium 60 or endocardium 58 and the links of support structure 20, as shown in FIG. 13C. Spacers 90 are preferably thermally preformed sections in the support structure located at the anchors 52, or desired attachment point 22, such that the links of the support structure are biased away from the tissue surface 60 or 58.

The support structure does not move relative to the tissue surface 60 or 58 at the anchors and/or attachment points; therefore, the support structure may directly contact the tissue surface at those locations, realizing that the support structure will endothelialize or epithelialize at the locations where the support structure is in intimate tissue contact. For support structures that completely reflect motion of the heart throughout the surface of the support structures, the entire support structure may be placed into intimate contact with the tissue surface 60 or 58 and allowed to epithelialize or endothelialize and become integral with the heart.

The harvested biological material is preferably a section of the pericardium, which may be cut away, sized relative to the heart support structure, and positioned between the support structure and the epicardium. Other tissue such as submucosal tissue (e.g., that obtained from the small intestine or other body organ) may be harvested, formed into the desired geometry, and used as the heart interface. The use of submucosal tissue is described in WO 98/19719 by Geddes, et al, entitled "Myocardial Graft Constructs", the entirety of which is incorporated herein by reference. Other biological materials such as collagen may alternatively be formed into the desired geometry and used as the heart interface.

The primary advantage of using biological tissue interface materials over currently available synthetic materials is the reduction in adhesions, thrombosis for tissue interfaces that are exposed to blood flow, or other tissue response that may adversely impact the function of the heart support structure. However, the heart support structure embodiments of the invention are equally effective at utilizing all types of tissue interface materials, biological and synthetic.

Synthetic tissue interface materials may be manufactured by extruding, injection molding, weaving, braiding, or dipping polymers such as PTFE, expanded PTFE, urethane, polyamide, polyimide, nylon, silicone, polyethylene, polyester, PET, composites of these representative materials, or other suitable graft material. These materials may be fabricated into a sheet, tubing, or other three-dimensional geometry using one or a combination of the stated manufacturing processes. Tubing materials may be along at least one side to form a flattened profile. The synthetic bypass graft may be coated, deposited, or impregnated with materials, such as parylene, heparin solutions, hydrophilic solutions, thromboresistance substances (e.g., glycoprotein IIb/IIIa inhibitors), antiproliferative substances (e.g., Rapamycin), or other substances designed to reduce adhesions, thrombosis (for heart interfaces exposed to blood flow), or mitigate other risks that potentially decrease the functionality of the heart support structure. In addition, synthetic bypass grafts may be seeded with endothelial cells or other biocompatible materials that further make the inner surface of the bypass graft biologically inert.

Deployment Systems

Surgical positioning and securing of the heart support structures described above to the epicardial tissue surface 60 involves a relatively large incision through the thoracic cavity to expose the heart. Surgical intervention enables accurate positioning and assures optimal securing of the support structure relative. During open heart surgery, direct access to the epicardial surface of the heart enables suturing or adhesively bonding the support structure to the heart; as such, alternative anchoring mechanisms described above are not necessarily required. However, such anchoring mechanisms may provide benefit in reducing the time to attach the support structure to the surface of the heart or improve the expanded (or contracted) orientation of the support structure relative to the end, diastolic (or end-systolic) orientation of the heart.

The support structure embodiments discussed in this invention are directly amenable to less invasive (i.e. minimally invasive) surgery involving a thoracostomy or mini median sternotomy to access the heart and endoscopes to visualize the thoracic cavity.

The deployment system for such reduced access surgical applications leverages conventional port access techniques to produce an opening through the thoracic cavity. Trocars are commonly used to gain access into the thoracic cavity after puncturing through the intercostal space. Once the ports into the thoracic cavity are defined, the parietal pericardium is cut and the incision is extended to expose the epicardial surface of the heart. As previously stated, the pericardium may be used as the tissue interface between the support structure and the epicardial surface of the heart.

The support structure is compressed into a reduced diameter by rolling for relatively planar support structures, or folding, stretching, or otherwise bending for more three-dimensional support structures. The compressed support structure is positioned in a delivery sheath designed to feed the support structure past the port. Once inside the thoracic cavity, the support structure is expelled from the delivery sheath, at which point it expands towards its preformed resting shape.

At this point, the support structure is lined up relative to the desired epicardial location and individual anchors are positioned through the tissue surface to secure the support structure to the tissue surface at each attachment point. As previously stated, alternative securing modalities may be used including adhesives, suture, thermal coagulation, implantable clips, staples, or other mechanism.

Conventional forceps, hemostats, and clamps are used to position the anchors. Alternatively, delivery tubes may compress the anchor pins into a reduced diameter for insertion through the tissue surface. In such a case, the delivery tubes are beveled at their distal ends to penetrate through the tissue surface and to provide a conduit to insert the anchor and position the anchor pin or pins into the myocardium.

When positioning the individual anchors at each attachment point, the support structure is continuously lined relative to the epicardial surface and at end-diastole and the anchors are inserted through the tissue surface. This ensures the support structure is positioned in its expanded orientation against the ventricles in their expanded orientation producing a better match between the expansion and contraction properties of the support structure to that of the ventricles. When lining the anchors of the support structure, the support links may need to be stressed or preformed into their expanded orientation to ensure the support links are appropriately lined up relative to the end-diastolic heart. As previously stated, the support structure may alternatively be attached to the heart during end-systole; at which case, the support structure is stressed or preformed into its contracted orientation during the attachment process. Alternatively, the heart may be temporarily stopped while securing sections of the support structure to the epicardial surface.

When positioning the support structures against the endocardial surface, catheters are used to compress the support structure into a reduced diameter. The catheters may be inserted percutaneously into the venous or arterial vasculature and routed to the desired heart chamber. To access the left ventricle, a catheter is routed through the femoral or brachial artery, around the aorta, past the aortic valve and into the left ventricle. Alternatively, the catheter is passed through the femoral or subclavian vein, into the right atrium, past the interatrial septum (by use of a transseptal technique), into the left atrium, past the mitral valve annulus, and into the left ventricle. To access the right ventricle, the catheter is passed through the femoral or subclavian vein, into the right atrium, past the tricuspid valve, and into the right ventricle.

Once in the desired heart chamber, the catheter is positioned at the apex of the ventricle. The support structure is compressed within the catheter by folding, stretching, or otherwise bending the support structure prior to inserting the catheter to the desired heart chamber. The support structure forms a three-dimensional geometry that closely matches the endocardial surface (either at end-diastole or end-systole). The anchors of the support structure may contain flaps intended to become entangled in the trabecula of the ventricles or anchor pins capable of becoming constrained in the myocardium once the anchor has penetrated through the endocardial surface. A plunger, in the form of a second steerable catheter, may be used to urge the anchors into position. Alternatively, the delivery catheter may be used as the plunger.

If any are used, the sheath and dilators of the deployment systems may be constructed from polyethylene, polycarbonate, thermoplastic (such as PEEK, manufactured by Victrex PLC, United Kingdom), other polymer, metal, or metal alloy that may be extruded, injection molded, or swaged into a tube having the desired cross-sectional profile. A taper and radius may be formed in the components of the deployment system by thermally forming the tubing into the desired shape or incorporating such features in the injection molding cast. In addition, the components of the deployment system may incorporate a softer distal tip fabricated by thermally bonding a short section of lower durometer tubing to the sheath or tapering the thickness of the sheath tubing.

To prevent the backflow of blood through deployment sheaths, hemostatic valves may be used. The hemostatic valves prevent blood leakage but permit insertion of the support structure through the sheath.

Electromagnetic Assist

It is within the scope of this invention to provide electromagnetic assist devices that take advantage of the characteristics of the heart support structure of the invention to impart contraction throughout the heart or along a specific region of the ventricles. These devices strategically induce magnetic fields throughout the heart support structure to impart an expansion or contraction of the heart support structure, which then transfers energy to the heart chambers.

The electromagnetic assist device may function independent from the natural contraction of the heart chambers to completely control the timing of isovolumetric ventricular contraction, systolic ejection, isovolumetric relaxation, and diastolic filling. Alternatively, the electromagnetic assist device may be synchronized to the inherent electrical propagation of the heart, which passes from the SA Node through the atria along the AV Node and through the ventricles. In doing so, the electromagnetic assist device times each phase of the cardiac cycle, as artificially created using the heart support structure, relative to the inherent electrical propagation of adjacent cardiac tissue, thereby preserving the natural motion of the heart and responding to biological stimuli for changing heart rate.

Figure 15A:
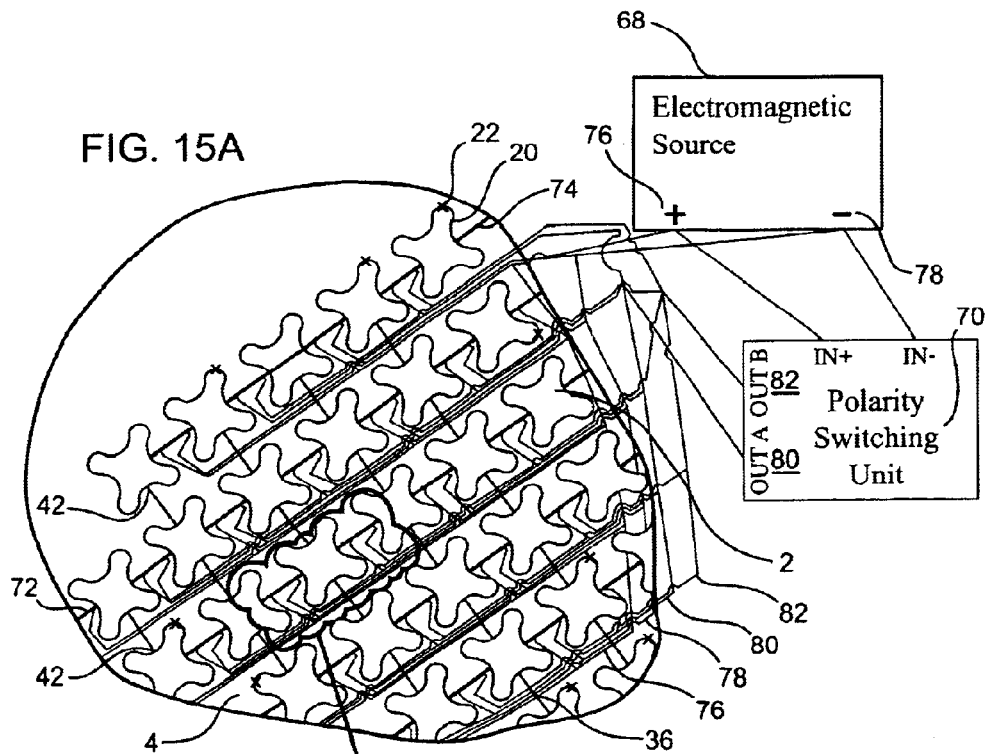
FIG. 15A is a side view of a heart containing an electromagnetically induced assist device that incorporates a heart support structure.

FIG. 15A shows a heart containing a support structure 20 that incorporates electromagnetic coils 72 strategically positioned throughout the links of the support structure. The embodiment of FIG. 15A is the same as that of FIGS. 9A and 9B. Alternatively, previously described support structures may be used, provided they incorporate links to which the electromagnetic coils 72 may be attached and used to induce a magnetic field designed to impart a contraction or expansion of the support structure.

U.S. Pat. No. 6,099,460 to Denker, incorporated herein by reference in its entirety, a heart that is artificially forced to contract in response to magnetic fields induced by electromagnets positioned on the exterior surface of the heart and/or interior of the heart. The '460 patent does not incorporate a support structure to provide optimal contraction and expansion, but relies solely on the attraction of the electromagnets positioned on opposite sides of the heart chambers. In addition the injured or diseased tissue contracts differently than viable tissue thus continuing to propagate the tissue remodeling of the injured or diseased tissue. In addition, the '460 patent does not teach assisting in the diastolic filling of the heart, and therefore excludes one important phase in the cardiac cycle.

Figure 15B:
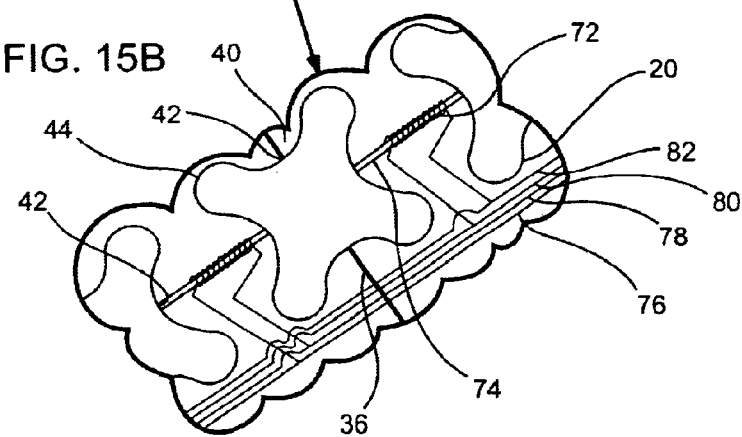
FIG. 15B is an enlarged view of the heart support structure in FIG. 15A.

Electromagnetic cores 74 are positioned over horizontal links 38 of support structure 20, as shown by an enlarged view of the support structure in FIG. 15B. Electromagnetic coils 72 are wound around electromagnetic cores 74 and are routed to electromagnetic source 68 either directly or via polarity switching unit 70 as shown in FIG. 15A. The leads of electromagnetic coils 72 that are directly connected to the electromagnetic source are either connected to the positive terminal 76 via positive lead 76 signal wires or the negative terminal 78 via negative lead 78 signal wires. The leads of electromagnetic coils 72 that are connected to the polarity switching unit 70 are either connected to OUTA terminal 80 via lead (A) 80 signal wires or the OUTB 82 terminal via lead (B) 82 signal wires. Polarity switching unit 70 is connected to the positive and negative terminals of electromagnetic source 68. The polarity switching unit and the electromagnetic source may also be grounded together. Polarity switching unit 70 changes the OUTA connection from the IN+ (that is routed to the positive terminal) to the IN− (that is routed to the negative terminal) and vice versa. Simultaneously, polarity switching unit 70 changes the OUTB connection from the IN− to the IN+ and vice versa. In switching the positive and negative connections of an electromagnetic coil 72, the induced magnetic field along the electromagnetic coil alters its polarity accordingly. As such, the response of adjacent coils to the specific polarity protocol may be specified to selectively produce an attraction between adjacent electromagnets, thereby causing a contraction of the heart support structure, or to induce a repulsion between adjacent electromagnets thereby causing an expansion of the heart support structure. The ability to switch the polarity of at least one set of electromagnetic coils 72 enables producing both an attraction and a repulsion thereby covering the complete cardiac cycle. The embodiment shown in FIG. 15A maintain the polarity of a group of electromagnetic coils 72 constant and changes the polarity of adjacent electromagnetic coils 72 to impart the attraction or repulsion force.

The period and amplitude of each pulse transmitted from the electromagnetic source (directly or via the polarity switching unit) to the electromagnetic coils determines the amount and duration of the attraction or repulsion force imparted to heart support structure 20 by the electromagnetic assist device. Support structure 20 is essential to the electromagnetic assist device in that it provides enhanced control to and enables variability in the expansion and contraction throughout the surface of the heart. Changing the stiffness profile of the support structure 20 throughout the surface of the heart is more sensitive and effective than varying the degree of attraction and repulsion between adjacent magnets.

Figures 16A, 16B:
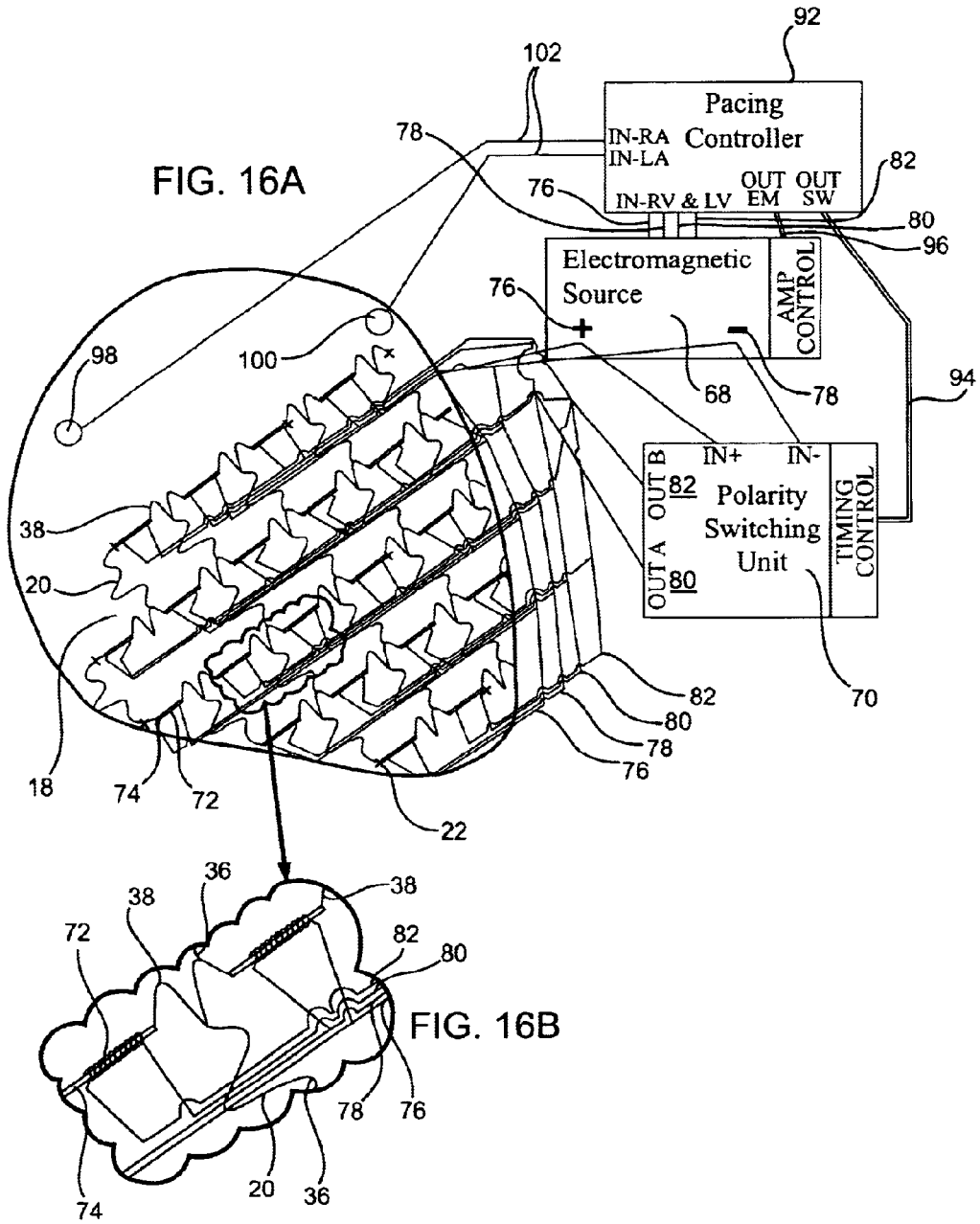
FIG. 16A is a side view of a heart containing an electromagnetically induced assist device that incorporates a heart support structure and is synchronized with the heart's electrical propagation.
FIG. 16B is an enlarged view of the heart support structure in FIG. 16A.

FIG. 16A shows a heart incorporating another electromagnetic assist device embodiment. This embodiment has a different support structure 20 embodiment attached only around the injured or diseased tissue. As such, the response of the electromagnetic assist device must be synchronized with the inherent electrical propagation throughout the heart. FIG. 16B shows an enlarged view of the heart support structure in FIG. 16A. Support structure 20 incorporates horizontal links 38 and vertical links 36 that interconnect electromagnetic cores 74 and associated electromagnetic coils 72. As described above, leads (76, 78, 80, or 82) of electromagnetic coils 72 are routed to terminals (positive or negative) on electromagnetic source 68 or to terminals (OUTA or OUTB) on polarity switching unit 70, which are routed to the terminals (positive or negative) on the electromagnetic source 68.

As shown in FIG. 16A, a pacing controller 92 is connected to amplitude control 96 of the electromagnetic source 68 and timing control 94 of polarity switching unit 70. Electrodes 98 and 100 are secured to the right atrium and left atrium respectively and atrial signals are transmitted to pacing controller 92 which can acquire the atrial electrograms. Ventricular signals from electromagnetic coils 72 may be transmitted through electromagnetic source 68 and/or polarity switching unit 70 to pacing controller 92 which can filter the ventricular electrograms. Pacing controller 92 utilizes the atrial and ventricular electrograms to determine the activation of heart support structure 20 by controlling the amplitude of the electromagnetic source and the switching of the magnetic field polarity. In this way, the contraction and expansion of the heart support structure may be synchronized with the natural movement of the heart.

Other Artificial Assists

The heart support structure embodiment shown in FIGS. 9A and 9B is described as a potential support structure for the electromagnetic assist device shown in FIG. 15A. This support structure embodiment may also be used in an assist device where an artificial external force other than electromagnetic induction is used. The predetermined response between the expansion (or contraction) of the width (or length) and the corresponding expansion (or contraction) of the length (or width) makes this support structure particularly amenable to an artificial external force that expands and/or contracts a first dimension and relies on the support structure to impart the expansion or contraction force to a second dimension. Of course, the first dimension and/or the second dimension described above may vary throughout the support structure. A linearly actuated external force may be used to expand or contract a discrete section of the support structure, relying on the support structure to transfer the expansion or contraction energy throughout the remaining support structure.

One such artificial external force involves attaching a length of skeletal tissue to a section of the support structure and causing the skeletal tissue to contract and relax in response to pacing stimuli. This linear contraction and expansion is transferred throughout the entire support structure to impart the desired three-dimensional contraction and expansion responses.

Another artificial external force involves any type of motor capable of exerting a linear force in response to an electrical current. The motor should be capable of miniaturization to fit inside an implantable device and operate under battery power such that the battery life lasts for years.

This invention has been described and specific examples of the invention have been portrayed. The use of those specific examples is not intended to limit the invention in any way. Additionally, to the extent that there are variations of the invention which are within the spirit of the disclosure and yet are equivalent to the inventions found in the claims, it is our intent that those claims cover those variations as well.

We claim as our invention:

1. An apparatus for treating a heart, at least a portion of which comprises a region of less viable or non-viable heart tissue, said apparatus comprising:
    at least one peripheral links disposable on at least one region of viable heart tissue; and
    a plurality of support links disposable on the region of less viable or non-viable heart tissue, each said support link being configured for attachment to either a said at least one peripheral link or another of said support links, wherein at least one of said support links is further configured for attachment to the region of less viable or non-viable heart tissue;
    wherein said at least one peripheral link is configured to move coincident with the contraction and dilation of the region of viable heart tissue and wherein said support links are configured to cause a corresponding movement of the region of less viable or non-viable heart tissue in response to said movement of said peripheral links.

2. The apparatus of claim 1, wherein said at least one peripheral link comprises a plurality of peripheral links wherein each said peripheral link is configured for connecting to either a support link or another of said peripheral links, wherein at least one of said peripheral links is further configured for attachment to the region of viable heart tissue; wherein said plurality of peripheral links are arranged to substantially surround the region of less viable or non-viable heart tissue.

3. The apparatus of claim 2, wherein said plurality of peripheral links are arranged wherein said plurality of peripheral links do not substantially surround the region of less viable or non-viable heart tissue.

4. The apparatus of claim 2, wherein said plurality of peripheral links are connected to each other.

5. The apparatus of claim 2, wherein said plurality of peripheral links are not connected to each other.

6. The apparatus of claim 2, wherein each said support link extends between two opposing peripheral links.

7. The apparatus of claim 1, wherein at least two support links intersect each other.

8. The apparatus of claim 7, wherein said at least two intersecting support links are interlocking.

9. The apparatus of claim 7, wherein said apparatus is attached to said heart at the point of intersection between said at least two support links.

10. The apparatus of claim 2, wherein said plurality of support links do not intersect each other.

11. The apparatus of claim 1, wherein each said support link has a proximal end and a distal end wherein said proximal ends are connected to each other at a central region of said apparatus.

12. The apparatus of claim 11, wherein each said support link is connected to said peripheral link at said distal end.

13. The apparatus of claim 11, wherein said central region is attached to said heart.

14. The apparatus of claim 2, further comprising groups of said plurality of support links, wherein each said support link has a proximal end and a distal end and wherein support links of a group are serially connected to each other wherein the distal end of one said support link is connected to the proximal end of an adjacent support link, each said connection point defining a node.

15. The apparatus of claim 14, wherein each of said groups of said plurality of support links extends radially outward from a central region of said apparatus.

16. The apparatus of claim 14, wherein the distance between adjacent nodes is constant.

17. The apparatus of claim 14, wherein adjacent support links define an angle at said node, wherein said angle is constant for each said node.

18. The apparatus of claim 14, wherein each said group of support links defines a sinusoidal pattern.

19. The apparatus of claim 15, wherein the length of said plurality of support links of each said group increases progressively from said central region to a peripheral region of said apparatus.

20. The apparatus of claim 2, wherein the lengths of said plurality of peripheral links are substantially the same.

21. The apparatus of claim 2, wherein said plurality of peripheral links have substantially the same lengths.

22. The apparatus of claim 2, wherein said plurality of peripheral links have varying lengths.

23. The apparatus of claim 2, wherein said plurality of peripheral links have substantially the same shape.

24. The apparatus of claim 1, wherein said plurality of peripheral links have varying shapes.

25. The apparatus of claim 1, wherein said plurality of support links have substantially the same lengths.

26. The apparatus of claim 1, wherein said plurality of support links have varying lengths.

27. The apparatus of claim 1, wherein said plurality of support links have substantially the same shapes.

28. The apparatus of claim 1, wherein said plurality of support links have varying shapes.

29. The apparatus of claim 1, wherein said plurality of support links have substantially the same widths.

30. The apparatus of claim 1, wherein said plurality of support links have varying widths.

31. The apparatus of claim 1, further comprising a central region comprising a compliant material.

32. The apparatus of claim 29, wherein said compliant material is selected from the group comprising silicone, urethane and a biologic material.

33. The apparatus of claim 1, wherein said apparatus has a substantially planar configuration.

34. The apparatus of claim 33, wherein the region of less viable or non-viable heart tissue is at a ventricular wall.

35. The apparatus of claim 1, wherein said apparatus has a substantially conical configuration.

36. The apparatus of claim 35, wherein the region of less viable or non-viable heart tissue is at an apical wall.

37. The apparatus of claim 2, wherein said plurality of peripheral links and said plurality of support links form interconnected cells.

38. The apparatus of claim 37, wherein said interconnected cells comprise hinges.

39. The apparatus of claim 37, wherein said cells have a width and a length and wherein one or both of said width and said length are selected to optimize said movement of said plurality of peripheral links and said movement of said plurality of support links.

40. The apparatus of claim 1, wherein said apparatus is configured for placement on an epicardial surface of said heart.

41. The apparatus of claim 1, wherein said apparatus is configured for placement on an endocardial surface of said heart.

42. The apparatus of claim 1, wherein said apparatus is comprised of a material selected from the group consisting of superelastic alloys, stainless steel, superelastic polymers, and any combinations thereof.

43. The apparatus of claim 42, wherein said superelastic alloy comprises nickel-titanium.

44. The apparatus of claim 1, further comprising a coating covering at least a portion of the apparatus.

45. The apparatus structure of claim 44, wherein said coating comprises a material selected from the group consisting of thermoplastics, thermoset plastics, silicone, parylene, heparin, thromboresistance substances, antiproliferative substances, platinum, gold, tantalum, tin, tin-indium, zirconium, zirconium alloys, zirconium oxide, zirconium nitrate, phosphatidyl-choline, and pyrolytic carbon.

46. A system for treating a heart, at least a portion of which comprises a region of less viable or non-viable heart tissue, said apparatus comprising:
  the apparatus of claim 1; and
  means for attaching the apparatus to the heart.

47. The system of claim 46, further comprising a tissue interface member for positioning between the apparatus and a surface of the heart.

48. The system of claim 47, wherein said tissue interface member comprises a synthetic material.

49. The system of claim 48, wherein said synthetic material comprises a biologically inert coating selected from the group consisting of parylene, heparin solutions, hydrophilic solutions, thromboresistance substances, antiproliferative substances, and endothelial cells.

50. The system of claim 47, wherein said tissue interface member is lubricious.

51. The system of claim 47, wherein said tissue interface member comprises a biologic material.

52. The system of claim 51, wherein said biologic material comprises one of the group consisting of pericardium, submucosal tissue and collagen.

53. The system of claim 46, wherein said attachment means comprises one or more of the group consisting of adhesives, coagulated tissue and a mechanical anchor.

54. The system of claim 53, wherein said mechanical anchor comprises one of the group consisting of a pin, a hook, a screw, a staple and a suture.

55. The system of claim 46, further comprising a means for delivering and deploying said apparatus through the chest wall of a patient.

56. The system of claim 46, further comprising a radiation source on said apparatus.

57. The system of claim 46, further comprising an electromagnetic assist device coupled to said apparatus.

* * * * *